US007642051B2

(12) United States Patent
Jacotot et al.

(10) Patent No.: US 7,642,051 B2
(45) Date of Patent: *Jan. 5, 2010

(54) SCREENING METHODS FOR THE IDENTIFICATION OF INHIBITORS OF HUMAN IMMUNODEFICIENCY VIRUS (HIV) VIRAL PROTEIN R (VPR) BINDING TO THE ADENINE NUCLEOTIDE TRANSLOCATOR (ANT)

(75) Inventors: Etienne Daniel Francois Jacotot, Paris (FR); Guido Kroemer, Paris (FR); Bernard Pierre Roques, Paris (FR); Lena Edelman, Boulogne (FR); Johan Hoebeke, Schiltigheim (FR); Catherine Brenner-Jean, Survilliers (FR); Anne-Sophie Belzacq, Margny-les-Compiégne (FR)

(73) Assignees: Institut Pasteur, Paris (FR); Institut National de la Sante et de la Recherche Medicale, Paris (FR); Centre National de la Recherche Scientifique, Paris (FR); Universite de Technologie de Compiegne, Compiegne (FR)

( * ) Notice: Subject to any disclaimer, the term of this patent is extended or adjusted under 35 U.S.C. 154(b) by 248 days.

This patent is subject to a terminal disclaimer.

(21) Appl. No.: 11/176,370

(22) Filed: Jul. 8, 2005

(65) Prior Publication Data
US 2006/0052285 A1 Mar. 9, 2006

Related U.S. Application Data

(63) Continuation of application No. 09/949,650, filed on Sep. 12, 2001, now Pat. No. 7,056,735.

(60) Provisional application No. 60/232,841, filed on Sep. 15, 2000, provisional application No. 60/231,539, filed on Sep. 11, 2000.

(51) Int. Cl.
C12Q 1/70 (2006.01)
G01N 33/53 (2006.01)
A61K 39/21 (2006.01)

(52) U.S. Cl. .................. 435/5; 435/7.1; 424/208.1
(58) Field of Classification Search .............. None
See application file for complete search history.

(56) References Cited

U.S. PATENT DOCUMENTS 6,013,858 A 1/2000 Wallace et al.
6,376,211 B1 * 4/2002 Little et al. ............ 435/21

FOREIGN PATENT DOCUMENTS

| EP | 0 911 341 A1 | 4/1999 |
|---|---|---|
| WO | WO 99/06588 | 2/1999 |
| WO | WO 99/07845 | 2/1999 |
| WO | WO 00/26370 | 5/2000 |
| WO | WO 00/42973 | 7/2000 |

OTHER PUBLICATIONS

Jacotot, E., et al., 2000, The HIV-1 Viral Protein R Induces Apoptosis via a Direct Effect on the Mitochondrial Permeability Transition Pore, J. Exp. Med. 191(1):33-45.*
Phizicky, E. M., and S. Fields, 1995, Protein-Protein Interactions: Methods for Detection and Analysis, Microbiol. Rev. 59(1):94-123.*
Philo, J. S., 1999, Overview of the Quantitation of Protein Interactions, Current Protocols in Protein Science, John Wiley & Sons, Inc., 20.1.1-20.1.13.*
Jacotot et al., "The HIV-1 viral protein R induces apoptosis via a direct effect on the mitochondrial permeability transition pore," *J. Exp. Med.*, 191(1):33-45, Jan. 3, 2000.
Jacotot et al., "Control of mitochondrial membrane permeabilization by adenine nucleotide translocator interacting with HIV-1 viral protein R and Bcl-1," *J. Exp. Med.*, 193(4):509-512, Feb. 19, 2001.
Jacotot et al., "Mechanism of mitochondrial membrane permeabilization by HIV-1 VPR, mimetics of Vpr and methods of screening active molecules having the ability to alter and/or prevent and/or mimic the interaction of VPR with ANT," Specification of U.S. Appl. No. 10/383,592, as filed on Mar. 10, 2003.
Aqeilan et al. *FEBS Lett.* 457:271-276 (1999).
Bauer et al., *J. Cell Biol.* 147:1493-1501 (1999).
Belzacq et al. *Cancer Research* 61:1260-1264 (2001).
Brandolin et al., *J. Bioenerg. Biomembr.* 25:459-472 (1993).
Brenner et al., *Oncogene* 19:329-336 (2000).
Bukrinsky et al., *Rev. Med. Virol.* 9:39-49 (1999).
Brustovetsky et al., *Biochemistry* 35:8483-8488 (1996).
Cheng et al., *Proc. Natl. Acad. Sci. USA* 94:690-694 (1997).
Ciminale et al., *Oncogene* 18:4505-4514 (1999).
Costantini et al., *Oncogene* 19:307-314 (2000).
Crompton, *Biochem. J.* 341:233-249 (1999).
Derfuss et al., *J. Virol.* 72:5897-5904 (1998).
Desagher et al., *J. Cell Biol.* 144:891-901 (1999).
Ellerby et al., *Nature Med.* 5:1032-1038 (1999).
Emerman et al., *Science* 280:1880-1884 (1998).
Ferri et al., *Ann. N. Y. Acad. Sci.* 926:149-165 (2000).
Frankel et al., *Annu. Rev. Biochem* 67:1-25 (1998).
Fulda et al., *J. Biol. Chem.* 273:33942-33948 (1998).
Goldmacher et al., *Proc. Natl. Acad. Sci. USA* 96:12536-12541 (1999).
Green et al., *Science* 281:1309-1312 (1998).
Gross et al., *Genes Dev.* 13:1899-1911 (1999).
Han et al., *Oncogene* 17:2993-3005 (1998).
Klingenberg et al., *Membrane Biol.*56:97-105 (1980).
Klingenberg, *J. Bioenerg. Biomembr.* 25:447-457 (1993).
Kroemer et al., *Nat. Med.*6:513-519 (2000).
Kroemer et al., *Immunol. Today* 18:44-51 (1997).
Larochette et al., *Exp. Cell Res.* 249:413-421 (1999).

(Continued)

Primary Examiner—Jeffrey S. Parkin
(74) Attorney, Agent, or Firm—Finnegan, Henderson, Farabow, Garrett & Dunner, L.L.P.

(57) ABSTRACT

The invention is directed to the induction of mitochondrial membrane permeabilization via the physical and functional interaction of the HIV-1 Vpr protein with the mitochondrial inner membrane protein ANT (adenine nucleotide translocator, also called adenine nucleotide translocase or ADP/ATP carrier). Reagents and methods for inducing and/or inhibiting the binding of Vpr to ANT, mitochondrial membrane permeabilization, and apoptosis are provided.

12 Claims, 16 Drawing Sheets

OTHER PUBLICATIONS

Lemasters et al., *Biochim. Biophys. Acta* 1366:177-196 (1998).
Macreadie et al., *Proc. Natl. Acad. Sci. USA* 92:2770-2774 (1995).
Macreadie et al., *FEBS Lett.* 410:145-149 (1997).
Marchetti et al., *Cancer Res.* 59:6257-6266 (1999).
Marshall et al., *J. Virol.* 73:5181-5185 (1999).
Marzo et al., *Science* 281:2027-2031 (1998).
Muthami et al., *DNA and Cell Biology* 19:179-188 (2000).
Narita et al., *Proc. Natl. Acad. Sci. USA* 95:14681-14686 (1998).
Piller et al., *Proc. Natl. Acad. Sci. USA* 93:111-115 (1996).
Rahmani et al., *J. Virol.* 74:2840-2846 (2000).
Ravagnan et al., *Oncogene* 18:2537-2546 (1999).
Rustin et al., *J. Biol. Chem.* 271:14785-14790 (1996).
Schendel et al., *Cell Death Differ.* 5:372-289 (1998).
Schüler et al., *J. Mol. Biol.* 285:2105-2117 (1999).
Shimizu et al., *Nature* 399:483-487 (1999).
Shimizu et al., *Proc. Natl. Acad. Sci. USA* 97:3100-3105 (2000).
Stanley et al., *J. Biol. Chem.* 270:16694-16700 (1995).
Vander Heiden et al., *Nat. Cell Biol.* 1:E209-216 (1999).
Vieira et al., *Cell Death and Differentiation* 7:1146-1154 (2000).
Vieira et al., *Oncogene* 20:4305-4316 (2001).
Wallace, *Science* 283:1482-1488 (1999).
Zamzami et al., *Oncogene* 19:6342-6350 (2000).

\* cited by examiner

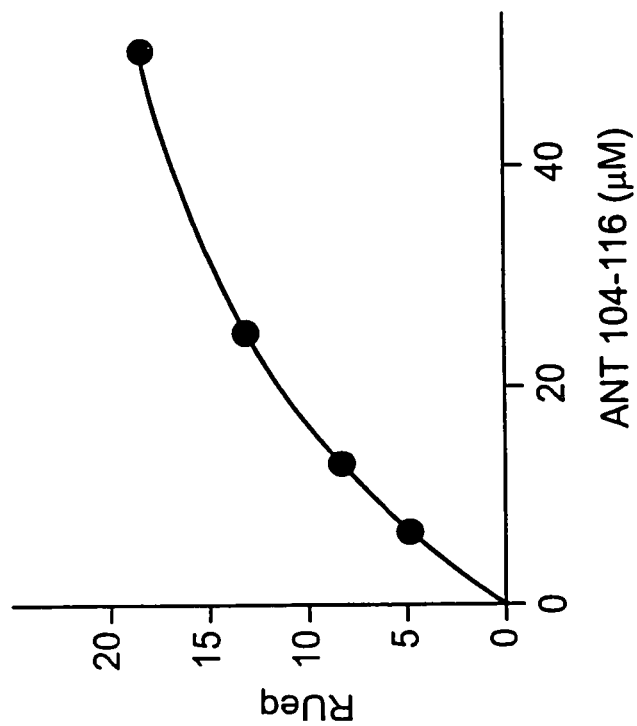
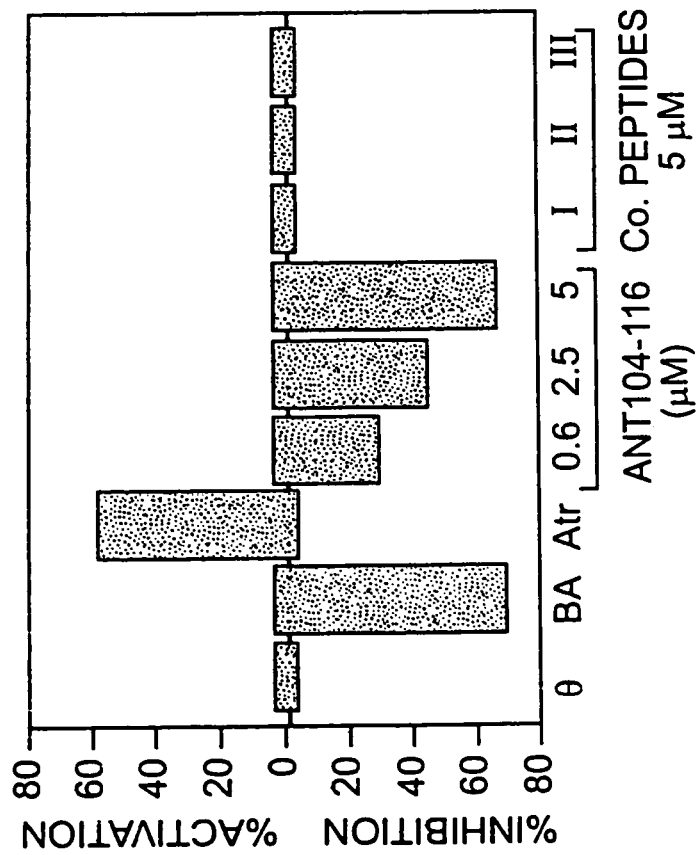
FIG. 1D
FIG. 1C

| PEPTIDE | RESPIRATORY CONTROL |
|---|---|
| Vpr1-51 | 5.1 |
| Vpr52-96 | 1.1 |
| Vpr1-96 | 2.0 |
| Vpr71-82 | 2.6 |
| NONE | 5.3 |

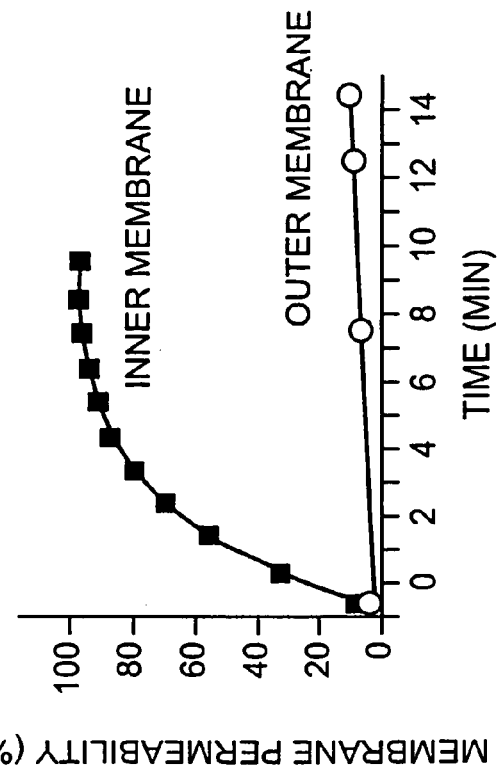
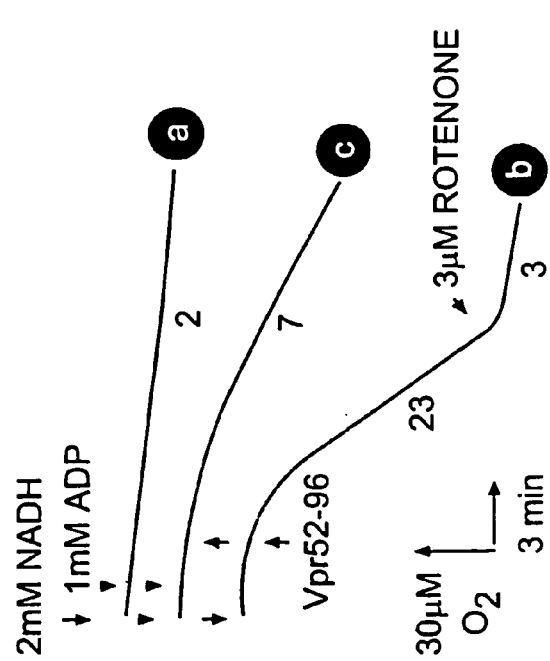
FIG. 5A
FIG. 5B
FIG. 5C

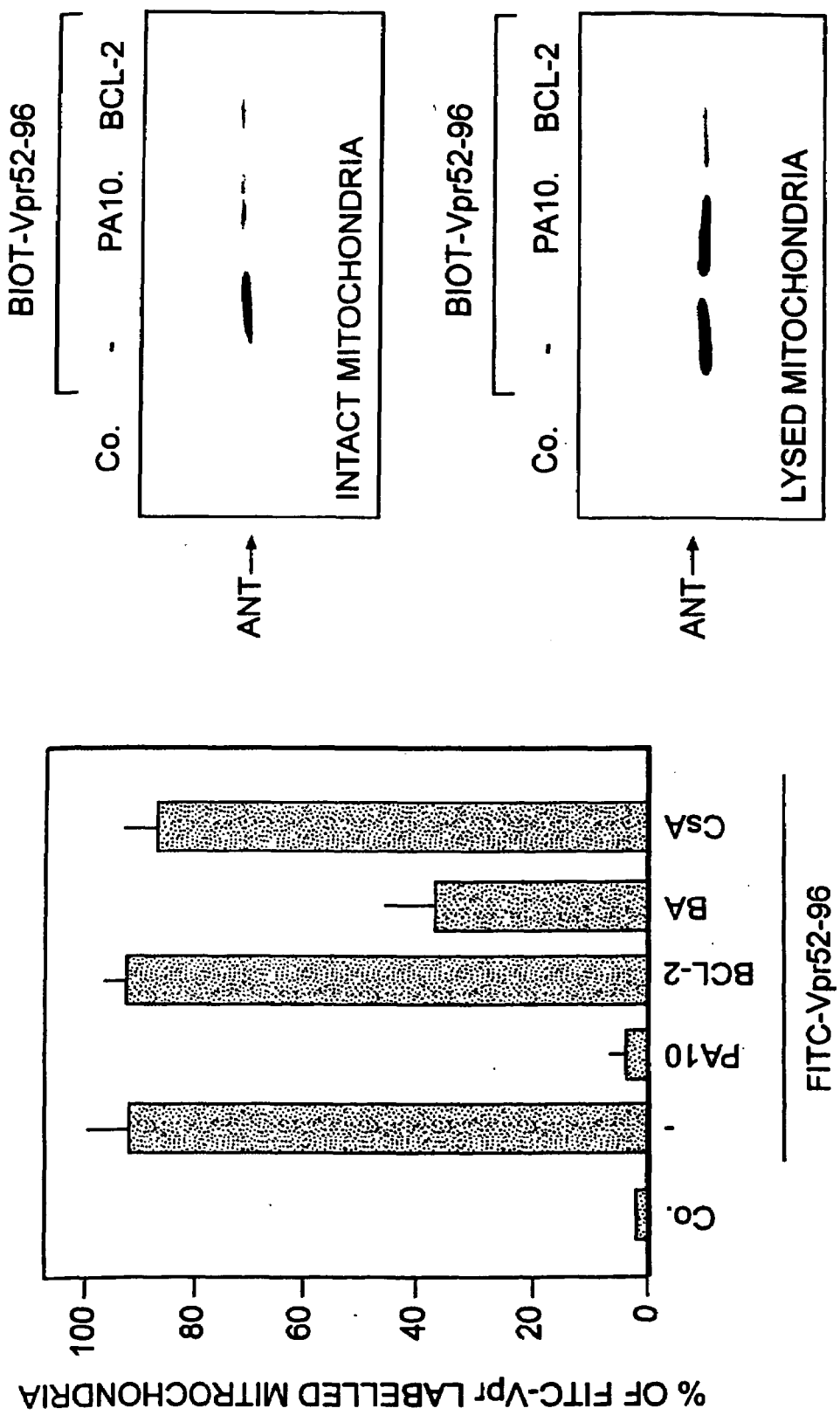

SEQUENCE LISTING

<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Lys Leu Ala Lys Leu Ala Lys Lys Leu Ala Lys Leu Ala Lys
 1               5                   10

<210> SEQ ID NO 2
<211> LENGTH: 12

```
<212> TYPE: PRT
<213> ORGANISM: Human immunodeficiency virus type 1

<400> SEQUENCE: 2

His Phe Arg Ile Gly Cys Arg His Ser Arg Ile Gly
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Lys Arg Thr Gln Phe Trp Arg Tyr Phe Ala Gly Asn
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Gln Asn Tyr Trp Gly His Lys Arg Phe Arg Asp Ala
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Gly His Lys Gln Phe Trp Gly Tyr Phe Ala Gly Asn
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Asn Met Leu Gly Glu Glu Asn Thr Tyr Leu Trp Arg
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg His Lys Gln Phe Trp Arg Tyr Phe Ala Gly Asn
 1               5                  10
```

SCREENING METHODS FOR THE IDENTIFICATION OF INHIBITORS OF HUMAN IMMUNODEFICIENCY VIRUS (HIV) VIRAL PROTEIN R (VPR) BINDING TO THE ADENINE NUCLEOTIDE TRANSLOCATOR (ANT)

CROSS-REFERENCE TO RELATED APPLICATIONS

This is a continuation of application Ser. No. 09/949,650, filed Sep. 12, 2001, now U.S. Pat. No. 7,056,735, and claims the benefit of U.S. provisional application Nos. 60/232,841, filed Sep. 15, 2000, and 60/231,539, filed Sep. 11, 2000, all of which are incorporated herein by reference.

BACKGROUND OF THE INVENTION

1. Field of the Invention

The invention is directed to discovery that the proapoptotic HIV-1-encoded protein Vpr induces mitochondrial membrane permeabilization via its physical and functional interaction with the mitochondrial inner membrane protein ANT (adenine nucleotide translocator, also called adenine nucleotide translocase or ADP/ATP carrier). HIV-1 Viral protein R (Vpr) interacts with the permeability transition pore complex (PTPC) to trigger ANT pore formation and/or mitochondrial membrane permeabilization (MMP) and consequent cell death (by apoptosis or any related mechanism of cell death).

2. Background

It is now recognized that mitochondria play an important role in controlling the life and death (the apoptosis) of cells (Kroemer and Reed 2000). Thus it seems that a growing number of molecules are involved in signal transduction, and that many metabolites (and certain viral effectors) act on the mitochondria and influence the permeabilization of mitochondrial membranes. Also, a certain number of experimental anti-cancer drugs kill cells by acting directly on mitochondrial membranes (Ravagnan et al., 1999; Larochette et al., 1999; Marchetti et al., 1999; Fulda et al., 1999; Belzacq et al., 2000). Therefore, the use of specific pro-apoptotic agents for mitochondria seems to be a concept that is emerging in anticancer chemotherapy (for reference: Costantini, et al., 2000). A possible outcome could be the use of cytoprotective molecules to treat illnesses associated with excess apoptosis (AIDS, neurodegenerative diseases, etc.) owing to their ability to stabilize mitochondrial membranes. Against this background, the identification (mode of action) of those molecular components that control the permeability of the mitochondrial membranes has become a major topic in biomedicine.

MMP is a key event of apoptotic cell death associated with the release of caspase activators and caspase-independent death effectors from the intermembrane space, dissipation of the inner transmembrane potential ($\Delta\Psi m$), as well as a perturbation of oxidative phosphorylation G. Kroemer, N. Zamzami, S. A. Susin, Immunol. Today 18, 44-51 (1997). D. R. Green, J. C. Reed, Science 281, 1309-1312 (1998). J. J. Lemasters, et al., Biochim. Biophys. Acta 1366, 177-196 (1998). D. C. Wallace, Science 283, 1482-1488 (1999). M. G. Vander Heiden, C. B. Thompson, Nat. Cell Biol. 1, E209-E216 (1999). A. Gross, J. M. McDonnell, S. J. Korsmeyer, Genes Dev. 13, 1988-1911 (1999). G. Kroemer, J. C. Reed, Nat. Med. 6, 513-519 (2000). Pro- and anti-apoptotic members of the Bcl-2 family regulate inner and outer MMP through interactions with the adenine nucleotide translocator (ANT; in the inner membrane, IM), the voltage-dependent anion channel (VDAC; in the outer membrane, OM), and/or through autonomous channel-forming activities G. Kroemer, N. Zamzami, S. A. Susin, Immunol. Today 18, 44-51 (1997). D. R. Green, J. C. Reed, Science 281, 1309-1312 (1998). J. J. Lemasters, et al., Biochim. Biophys. Acta 1366, 177-196 (1998). D. C. Wallace, Science 283, 1482-1488 (1999). M. G. Vander Heiden, C. B. Thompson, Nat. Cell Biol. 1, E209-E216 (1999). A. Gross, J. M. McDonnell, S. J. Korsmeyer, Genes Dev. 13, 1988-1911 (1999). G. Kroemer, J. C. Reed, Nat. Med. 6, 513-519 (2000). I. Marzo, et al., Science 281, 2027-2031 (1998). S. Shimizu, M. Narita, Y. Tsujimoto, Nature 399, 483-487 (1999). S. Shimizu, A. Konishi, T. Kodama, Y. Tsujimoto, Proc. Natl. Acad. Sci. USA 97, 3100-3105 (2000). S. Desagher, et al., J. Cell Biol. 144, 891-901 (1999).

ANT and VDAC are major components of the permeability transition pore complex (PTPC), a polyprotein structure organized at sites at which the two mitochondrial membranes are apposed. G. Kroemer, N. Zamzami, S. A. Susin, Immunol. Today 18, 44-51 (1997). D. R. Green, J. C. Reed, Science 281, 1309-1312 (1998). J. J. Lemasters, et al., Biochim. Biophys. Acta 1366, 177-196 (1998). D. C. Wallace, Science 283, 1482-1488 (1999). M. G. Vander Heiden, C. B. Thompson, Nat. Cell Biol. 1, E209-E216 (1999). A. Gross, J. M. McDonnell, S. J. Korsmeyer, Genes Dev. 13, 1988-1911 (1999). G. Kroemer, J. C. Reed, Nat. Med. 6, 513-519 (2000). M. Crompton, Biochem. J. 341, 233-249 (1999).

The adenine nucleotide translocator (ANT) plays an important role in the process that triggers the permeabilization of mitochondrial membranes, and subsequent apoptosis (Marzo, et al., 1998; Brenner, et al., 2000). In the cellular context, ANT is inserted into the internal membrane of mitochondria and has two opposing functions. On the one hand, ANT is a vital antiport for cellular bioenergetics and is specific to ATP and ADP. On the other hand, ANT can form a non-specific lethal pore through the action of certain ligands (natural or xenobiotic) that eliminate the mitochondrial electrochemical gradient.

The HIV-1 regulatory protein Vpr has pleiotropic effects on viral replication and cellular proliferation, differentiation, cytokine production, and NF-κB-mediated transcription. M. Emerman, M. H. Malim, Science 280, 1880-1884 (1998). A. D. Frankel, J. A. T. Young, Annu. Rev. Biochem. 67, 1-25 (1998). M. Bukrinsky, A. Adzhubei, J. Med. Virol. 9, 39-49 (1999). In addition, Vpr can localize to mitochondria. I. G. Macreadie, et al., Proc. Natl. Acad. Sci. USA 92, 2770-2774 (1995). I. G. Macreadie, et al., FEBS Lett. 410, 145-149 (1997). K. Muthami, L. J. Montaner, V. Ayyavoo, D. B. Weine, DNA and Cell Biology 19, 179-188 (2000). E. Jacotot, et al., J. Exp. Med. 191, 33-45 (2000). Full length (Vpr1-96) or truncated synthetic forms of Vpr act on the PTPC to induce all mitochondrial hallmarks of apoptosis, including $\Delta\Psi_m$ loss and the release of cytochrome c and apoptosis inducing factor (AIF). E. Jacotot, et al., J. Exp. Med. 191, 33-45 (2000). The MMP-inducing activity of Vpr resides in its C-terminal moiety (Vpr52-96), within an α-helical motif of 12 amino acids (Vpr71-82) containing several critical arginine (R) residues (R73, R77, R80) which are strongly conserved among different pathogenic HIV-1 isolates. L G. Macreadie, et al., Proc. Natl. Acad. Sci. USA 92, 2770-2774 (1995). I. G. Macreadie, et al., FEBS Lett. 410, 145-149 (1997). E. Jacotot, et al., J. Exp. Med. 191, 33-45 (2000).

Depending on the apoptotic stimulus, permeabilization may affect the OM and IM in a variable fashion and may or may not be accompanied by matrix swelling. G. Kroemer, N. Zamzami, S. A. Susin, Immunol. Today 18, 44-51 (1997). D. R. Green, J. C. Reed, Science 281, 1309-1312 (1998). J. J. Lemasters, et al., Biochim. Biophys. Acta 1366, 177-196

(1998). D. C. Wallace, *Science* 283, 1482-1488 (1999). M. G. Vander Heiden, C. B. Thompson, *Nat. Cell Biol.* 1, E209-E216 (1999). A. Gross, J. M. McDonnell, S. J. Korsmeyer, *Genes Dev.* 13, 1988-1911 (1999). G. Kroemer, J. C. Reed, *Nat. Med.* 6, 513-519 (2000). In vitro experiments performed on purified mitochondria or proteins reconstituted into artificial membranes suggest at least two competing models of MMP. On the one hand, pore formation by ANT has been proposed to account for IM permeabilization, osmotic matrix swelling, and consequent OM rupture, resulting because the surface area of the IM with its folded christae exceeds that of the OM. In support of this hypothesis, pro-apoptotic molecules such as Bax, atractyloside, $Ca^{2+}$, and thiol oxidants cause ANT (which normally is a strictly specific ADP/ATP antiporter) to form a non-specific pore (I. Marzo, et al., *Science* 281, 2027-2031 (1998); N. Brustovetsky, M. Klingenberg, *Biochemistry* 35, 8483-8488 (1996); C. Brenner, et al., *Oncogene* 19, 329-336 (2000)). On the other hand, VDAC has been suggested to account for a primary OM permeabilization not affecting IM (S. Shimizu, M. Narita, Y. Tsujimoto, *Nature* 399, 483-487 (1999). S. Shimizu, A. Konishi, T. Kodama, Y. Tsujimoto, *Proc. Natl. Acad. Sci. USA* 97, 3100-3105 (2000)). In favor of this hypothesis, the permeabilization of VDAC-containing liposomes to sucrose or cytochrome c is enhanced by Bax and inhibited by Bcl-2 in vitro. S. Shimizu, M. Narita, Y. Tsujimoto, *Nature* 399, 483-487 (1999). S. Shimizu, A. Konishi, T. Kodama, Y. Tsujimoto, *Proc. Natl. Acad. Sci. USA* 97, 3100-3105 (2000).

Recent studies have revealed the existence of several viral apoptosis inhibitors acting on mitochondria. For example, adenovirus, Epstein Barr virus, Herpes virus saimiri, and Kaposi sarcoma-associated human herpes virus 8 produce apoptosis-suppressive Bcl-2 homologs. E. H.-Y. Cheng, et al., *Proc. Natl. Acad. Sci. USA* 94, 690-694 (1997). J. H. Han, D. Modha, E. White, *Oncogene* 17, 2993-3005 (1998). T. Derfuss, et al., *J. Virol.* 72, 5897-5904 (1998). W. L. Marshall, et al., *J. Virol.* 73, 5181-5185 (1999). In addition, several viruses encode PTPC-interacting proteins without any obvious homology to the Bcl-2/Bax family. The cytomegalovirus apoptosis inhibitor pUL37x (V. S. Goldmacher, et al., *Proc. Natl. Acad Sci. USA* 96, 12536-12541 (1999).) and Vpr, an HIV-1-encoded apoptosis inducer, selectively bind to ANT. The proapoptotic p13 (II) protein derived from the X-II of HTLV-1 is also targeted to mitochondria via a peptide motif that bears structural similarities to the mitochondriotoxic domain of Vpr. V. Ciminale, et al., *Oncogene* 18, 4505-4514 (1999). Moreover, the pro-apoptotic, MMP-inducing hepatitis virus B protein X interacts with VDAC. Z. Rahmani, K. W. Huh, R. Lasher, A. Siddiqui, *J. Virol.* 74, 2840-2846 (2000). Thus, both VDAC and ANT emerge as major targets of viral apoptosis regulation and, perhaps, as targets for pharmacological intervention on viral pathogenesis and/or other pathologies linked to apoptosis dysregulations (i.e., cancer, ischemia, neurodegenerative diseases, etc.). Apoptosis is a process that develops in several phases: (1) an initiation phase, which is extremely heterogeneous and during which the biochemical pathways participating in the process depend on the apoptosis-inducing agent; (2) a decision phase, which is common to different types of apoptosis, during which the cell "decides" to commit suicide; and (3) a common degradation phase, which is characterized by the activation of catabolic hydrolases (caspases and nucleases). Although the activation of caspases (cysteine proteases cleaving at aspartic acid [Asp] residues) and nucleases is necessary for the acquisitions of the full apoptotic morphology, it appears clear that inhibition of such enzymes does not inhibit cell death induced by a number of different triggers: Bax, Bak, c-Myo, PML, FADD, glucocorticoid receptor occupancy, tumor necrosis factor, growth factor withdrawal, CXCR4 cross-linking, and chemotherapeutic agents, such as etoposide, camptothecin, or cisplatin. In the absence of caspase activation, cells manifest a retarded cytolysis without characteristics of advanced apoptosis, such as total chromatin condensation, oligonucleosomal DNA fragmentation, and formation of apoptotic bodies. However, before cells lyse, they do manifest a permeabilization of both mitochondrial membranes with dissipation of the inner transmembrane potential ($\Delta\psi_m$) and/or the release of apoptogenic proteins, such as cytochrome c and apoptosis-inducing factor (AIF) via the outer membrane. These results have invalidated the hypothesis that caspase activation is always required for apoptotic cell death to occur. Rather, cell death is intimately associated with the permeabilization of mitochondrial membranes.

The understanding of apoptosis has recently been facilitated by the development of cell-free systems. Instead of considering the cell as a black box, subcellular fractions (e.g., mitochondria, nuclei, and cytosol) are mixed together with the aim to reconstitute the apoptosis phenomenon by recapitulating the essential steps of the process in vitro. It appears that proapoptotic second messengers, whose nature depends on the apoptosis-inducing agent, accumulate in the cytosol during the initiation phase. These agents then induce mitochondrial membrane permeabilization, allowing cells to enter the decision phase. The apoptotic changes of mitochondria consist in a $\Delta\psi_m$ loss, transient swelling of the mitochondrial matrix, mechanical rupture of the outer membrane and/or its nonspecific permeabilization by giant protein-permanent pores, and release of soluble intermembrane proteins (SIMPs) through the outer membrane. Once the mitochondrial membrane barrier function is lost, several factors, e.g., the metabolic consequences at the bioenergetic level, the loss of redox homeostasis, and the perturbation of ion homeostasis, contribute to cell death. The activation of proteases (caspases) and nucleases by SIMP's is necessary for the acquisition of apoptotic morphology. This latter phase corresponds to the degradation step, beyond the point of no return of the apoptotic process. Different SIMPs provide a molecular link between mitochondrial membrane permeabilization and the activation of catabolic hydrolases: cytochrome c (a heme protein that participates in caspase activation), certain procaspases (in particular, procaspases 2 and 9, which in some cell types, are selectively enriched in mitochondria), and AIF. AIF is a nuclear-encoded intermembrane flavoprotein that translocates to the nucleus where it induces the caspase-independent peripheral chromatin condensation and the degradation of DNA into 50-kilobase pair fragments.

The mechanism of mitochondrial membrane permeabilization is not completely understood. Some investigators prefer the hypothesis that proapoptotic members of the Bcl-2 family are inserted in the outer membrane where they oligomerize and form cytochrome c permeant pores in an autonomous fashion, not requiring the interaction with other mitochondrial membrane proteins. However, Bax-induced membrane permeabilization is inhibited by cyclosporin A (CsA) and bongkrekic acid (BA), two inhibitors of formation of the permeability transition pore (or "megachannel"), suggesting that sessile mitochondrial proteins (the targets of CsA and BA) are involved in this process. The permeability transition pore has a polyprotein structure that is formed at the contact sites between the inner and outer membranes. One of the key proteins of the permeability transition pore complex (PTPC) is the adenine nucleotide translocator (ANT). ANT, the target of BA, is the most abundant inner membrane protein, ANT normally functions as a specific carrier protein for the exchange of adenosine triphosphate (ATP) and adenosine diphosphate (ADP), but it can become a nonspecific pore.

An interesting property of the PTPC is that the permeabilization of the inner and/or outer mitochondrial membranes compromises the bioenergetic equilibrium of the cell (e.g., it provokes the oxidation of reduced NADPH and glutathione, the depletion of ATP, and the dissipation of $\Delta\psi_m$ and effects the homeostasis of intracellular ions (e.g., by releasing $Ca^{2+}$ from the matrix). Intriguingly, all of these changes themselves increase the probability of PTPCs opening. This has two important implications. First, the consequences of PTPC opening themselves favor opening of the PTPC in a self-amplification loop that coordinates the lethal response among mitochondria within the same cells. Second, this implies that the final result of PTPC opening is a stereotyped ensemble of biochemical alterations, which does not depend on the initiating stimulus, be it a specific proapoptotic signal transduction cascade or nonspecific damage at the energy or redox levels.

Chemotherapy aims at the specific eradication of cancer cells, mostly through the induction of apoptosis. Gene therapy can employ Bax-delivering vectors, thereby indirectly targeting mitochondria to induce apoptosis. In contrast to such proteins, certain peptides readily penetrate the plasma membrane and thus can be used as true pharmacologic agents. Mastoparan, a peptide isolated from wasp venom, is the first peptide known to induce mitochondrial membrane permeabilization via a CsA-inhibitable mechanism and to induce apoptosis via a mitochondrial effect when added to intact cells. This peptide has an α-helical structure and possesses some positive charges that are distributed on one side of the helix. A similar peptide (KLAKLAKKLAKLAK or $(KLAKLAK)_2$ (K=lysine, L=leucine, and A=alanine) (SEQ ID NO:1) has been found recently to disrupt mitochondrial membranes when it is added to purified mitochondria, although the mechanisms of this effect have not been elucidated. (Ellerby, H. M. et al., Anti-cancer activity of targeted pro-apoptotic peptides, *Nature Med.* 5, 1032-1038 (1999)).

The proapoptotic 96 amino acid protein viral protein R (Vpr) from human immunodeficiency virus-I contains a comparable structural motif (aa 71-82), i.e., an α-helix with several cationic charges that concentrate on the same side of the helix. Vpr, as well as Vpr derivatives containing this "mitochondriotoxic" domain cause a rapid CsA and BA-inhibited dissipation of the $\Delta\psi_m$ as well as the mitochondrial release of apoptogenic proteins, such as cytochrome c or AIF. The same structural motifs relevant for cell killing appear to be responsible for the mitochondriotoxic effects of Vpr. Vpr favors the permeabilization of artificial membranes containing the purified PTPC or defined PTPC components such as the ANT combined with Bax, but this effect is prevented by the addition of recombinant Bcl-2. According to surface plasmon resonance studies, the Vpr C-terminus binds purified ANT with a high affinity in the nanomolar range. E. Jacotot et al., *J. Exp. Med.* 191, 33-45 (2000), which is specifically incorporated herein by reference. In addition, a biotinylated Vpr-derived peptide (Vpr52-96) may be employed as bait to specifically purify a mitochondrial molecular complex containing ANT and the VDAC. Yeast strains lacking ANT or VDAC are less susceptible to Vpr-induced killing than are control cells. Thus, Vpr induces apoptosis via a direct effect on the mitochondrial PTPC. In analogy to Vpr, the p13 (II) protein derived from the X-II open reading frame of HTLV-1 is targeted to mitochondria and can cause a dissipation of the $\Delta\psi_m$ and mitochondrial swelling. Mitochondrial targeting of this protein has been mapped to a decapeptide sequence that contains several Arg residues that are asymmetrically distributed in the α-helix. However, Arg-Ala substitutions within the mitochondriotoxic domain of p13 (II) did not abolish the mitochondrial targeting of p13.

Lethal peptides may be targeted to mitochondria and more specifically, at least in the case of Vpr, to the PTPC. Ellerby et al. recently have fused the mitochondriotoxic $(KLAKLAK)_2$ motif (SEQ ID NO:1) to a targeting peptide that interacts with endothelial cells. Such a fusion peptide is internalized and induces mitochondrial membrane permeabilization in angiogenic endothelial cells and kills MDA-MD-435 breast cancer xenografts transplanted into nude mice. Similarly, a recombinant chimeric protein containing interleukin 2 (IL-2) protein fused to Bax selectively binds to and kills IL-2 receptor-bearing cells in vitro. Thus, specific cytotoxic agents that target surface receptors, translocate into the cytoplasm, and induce apoptosis via mitochondrial membrane permeabilization might be useful in treating cancer.

A recurrent problem with conventional chemotherapeutic agents is that they exploit endogenous apoptosis-induction pathways that may be compromised by alterations such as mutations of p53, increased antioxidant activity, blockade of the CD95/CD95L pathway, overexpression of Bcl-2-like proteins, etc. One possible strategy to enforce cell death is to trigger downstream events of the common apoptotic pathway. Thus, adenovirus-mediated transfer of caspases has been proposed as one strategy to induce cell death beyond any regulation. An alternative strategy is to use mitochondriotoxic agents that induce cell death irrespective of the upstream control mechanisms and irrespective of the status of caspases and endogenous caspase inhibitors. As an example, LND, arsenite, or CD437 induce cell death independently of the p53 status via a pathway that is not affected by caspase inhibitors. Similarly, betulinic acid and Vpr trigger CD95 (Apo-1/Fas)- and p53-independent apoptosis, and both permeabilize mitochondrial membranes in a caspase-independent fashion. As a result, these types of agents may prove to be highly useful in killing normally resistant cells. Moreover, the future of tumor therapy may profit from the design of agents that overcome the Bcl-2-mediated stabilization of mitochondrial membranes as well as from targeting amphipathic peptides or peptidomimetics to defined cellular populations or tissues.

Selective eradication of transformed cells by use of mitochondrion-specific agents should be effective. One strategy is to target a toxic agent to selected cell types on the basis of the specific expression of surface receptors. Another, yet to be developed, strategy would aim at exploiting difference in the composition or regulation of the PTPC between normal and tumor cells. Future research will tell to which extent cell targeting (by use of retroviral or adenoviral vectors, use of integrin-specific domains, etc.) and/or targeting of tumor-specific alterations in the PTPC will prove to be useful in cancer therapy, and also in the treatment of neurodegenerative diseases hypothetically linked to mitochondrial dysfunction (i.e., Friedrich ataxia, Hereditary spastic paraplegia, Huntington disease, Amyotrophic lateral sclerosis, Parkinson disease, Alzheimer disease) and treatment of acute organ failure that may involve regulatory events acting at the level of MMP (i.e., ischemia) (Kroemer, G. et al., Mitochondrial control of cell death, *Nature Med.*, vol. 6, no. 5, 513-519 (1999)).

Thus, there exists a need in the art for methods and reagents for regulating mitochondrial permeabilization and apoptosis.

SUMMARY OF THE INVENTION

The present invention relates to the physical and functional interactions between Vpr and the adenine nucleotide translocator (ANT), which function to permeabilize mitochondrial membranes and result in the death of cells by apoptosis. In a preferred embodiment, the present invention relates to the physical and functional interactions between Vpr and the three human isoforms of ANT also designated ANT1, ANT2, and ANT3. The invention encompasses methods of exploiting this novel mechanism to permeabilize mitochondrial membranes. The invention further encompasses methods of causing cell death by apoptosis.

The invention also encompasses methods of altering or preventing binding of Vpr to ANT. The invention further encompasses methods of altering or preventing channel formation due to the association of Vpr with ANT. The invention also encompasses methods of causing or preventing permeabilization of mitochondrial membranes. The invention also encompasses methods of causing or preventing cell death by apoptosis.

The invention also encompasses methods of screening for molecules that alter or prevent binding of Vpr to ANT. The invention further encompasses methods of screening for molecules that alter or prevent channel formation due to the association of Vpr with ANT. The invention also encompasses methods of screening for molecules that cause or prevent permeabilization of mitochondrial membranes. The invention also encompasses methods of screening for molecules that cause or prevent cell death by apoptosis.

The invention also encompasses methods of screening for molecules that compete with the binding of the C-terminal moiety of Vpr (vpr52-96 for HIV-1) to ANT. The invention also encompasses methods of screening for molecules that promote the binding of the C-terminal moiety of Vpr (vpr52-96 for HIV-1) to ANT. The invention also encompasses methods of screening for molecules that alter or prevent binding of the C-terminal moiety of Vpr (vpr52-96 for HIV-1) to ANT. The invention further encompasses methods of screening for molecules that alter or prevent permeabilization of mitochondrial membranes due to the association of the C-terminal moiety of Vpr (vpr52-96 for HIV-1) with ANT. The invention further encompasses methods of screening for molecules that alter or prevent apoptosis due to the association of the C-terminal moiety of Vpr (vpr52-96 for HIV-1) with ANT.

The invention also encompasses peptidic or non-peptidic molecules that alter or prevent binding of Vpr to ANT. The invention also encompasses peptidic or non-peptidic molecules that mimic Vpr or Vpr fragment in its capacity to interact physically or functionally with ANT. The invention further encompasses peptidic or non-peptidic molecules that alter or prevent channel formation due to the association of Vpr with ANT. The invention also encompasses peptidic or non-peptidic molecules that cause or prevent permeabilization of mitochondrial membranes. The invention also encompasses peptidic or non-peptidic molecules that cause or prevent cell death by apoptosis. The invention further encompasses pharmaceutical and diagnostic compositions comprising these molecules and the use of these compositions to cause or prevent permeabilization of mitochondrial membranes or apoptosis.

The invention further encompasses peptidic or non-peptidic molecules that mimic the C-terminal moiety of Vpr (vpr52-96 for HIV-1) and modulate the permeabilization of mitochondrial membranes. The invention also encompasses peptidic or non-peptidic molecules that compete with the binding of the C-terminal moiety of Vpr (vpr52-96 for HIV-1) to ANT. The invention also encompasses peptidic or non-peptidic molecules that promote the binding of the C-terminal moiety of Vpr (vpr52-96 for HIV-1) to ANT. The invention further encompasses pharmaceutical and diagnostic compositions comprising these molecules and the use of these compositions to cause or prevent permeabilization of mitochondrial membranes or apoptosis.

The invention also encompasses methods for screening for genetic or epigenetic alterations in the expression or structure of the three ANT isoforms in humans. The invention further encompasses screening and diagnosis for differences in the ability of the three ANT isoforms in different patients to interact with Vpr and to promote mitochondrial membrane permeabilization, channel formation, and/or apoptosis.

The invention also encompasses methods for specific cell killing by induction of apoptosis.

The invention also encompasses methods for screening molecules modifying channel properties of ANT.

The invention further encompasses methods of screening of active molecules able to alter or prevent ANT-Bcl2 interaction.

By studying the cytotoxic properties of the Vpr protein of HIV-1, the inventors discovered that Vpr interacts directly with ANT to trigger the permeabilization of mitochondrial membranes, as well as apoptosis. First, Vpr goes through an external mitochondrial membrane using the mitochondrial protein (also called "voltage-dependent anion channel": VDAC) and then attaches itself to the ANT, its primary target, with strong affinity (KD=mM). The ANT/Vpr complex forms high-conductance channels that trigger the permeabilization of the internal mitochondrial membrane, the swelling of the mitochondrial matrix and, finally, the breakage of the external membrane, and thus the release of factors that implement apoptosis (e.g., AIF, cytochrome c and some pro-caspases). The inventors have identified interaction sites between ANT and Vpr: for Vpr (14 Kd; 96 aa), the binding site to ANT brings into play the pattern 71HFRIGCRHSRIG82 (minimal toxic pattern) (SEQ ID NO:2) in the heart of the linear structure (α-helicoidal between amino-acids 52 and 83) of Vpr 52-96. For ANT1 (30 Kd; 298 aa), the binding site to Vpr brings into play the pattern 104DRHKQFWRYFAGN116 (SEQ ID NO:7) in the middle of the second ANT ring (aa 92-116).

The inventors' discovery of the physical and functional interaction between Vpr and ANT, and of at least one of the interaction sites, led them to build analogs of said toxic pattern of Vpr that can interact with the protein complex (permeability transition pore; PTPC) that contains ANT. These molecules can serve to imitate the pro-apoptotic effect of Vpr in order to destroy cancerous cells in vitro or in vivo. These molecules are either peptide or non-peptide molecules and are acquired in isolated or purified form.

The present invention pertains to a novel protein/protein interaction between the retroviral HIV regulatory protein Vpr and the mitochondrial adenine nucleotide translocator (ANT) a membrane associated receptor implicated in the control of cell death by apoptosis. The invention also concerns peptidic or non-peptidic molecules having the ability to alter and/or to prevent the binding (or the channel formation due to this binding) of Vpr to ANT. Another aspect of the invention concern peptidic or non-peptidic molecules having the ability to mimic the C-terminal moiety of Vpr (Vpr52-96 for HIV-1) in its capacity to bind ANT and cooperate with ANT to permeabilise mitochondrial membranes (and consequently kill cells). The invention is also directed to pharmaceutical and diagnostic compositions containing an effective amount of the molecules altering and/or preventing the binding (and/or conformational consequences of this binding such as channel formation) of Vpr to ANT (consequently such compositions will be cytoprotectives), as well as to therapeutic or diagnostic methods using such pharmaceutical or diagnostic composition. Moreover, the invention is also directed to pharmaceutical and diagnostic compositions containing an effective amount of the molecules able to mimic the C-terminal part of Vpr in its capacity to bind and cooperate with ANT to permeabilise mitochondrial membranes (and consequently kill cells), as well as to therapeutic or diagnostic methods using such pharmaceutical or diagnostic composition. The invention also deals with methods of screening new active molecules (endogenous or xenobiotics) having the ability to alter and/or to prevent the binding (or the channel formation due to this binding) of Vpr to ANT, or having the ability to mimic the C-terminal moiety of Vpr (Vpr52-96 for HIV-1) in its capacity to bind ANT and cooperate with ANT to permeabilise mitochondrial membranes (and consequently kill cells). Finally the invention is directed to methods of screening genetics or epigenetics (such as specific modifications in cancer affected individuals) alterations in the expression or structure of the three ANT isoforms in humans.

Thus, the present invention concerns a protein-to-protein interaction between Vpr and ANT, and potentially between Vpr and VDAC, which can exploited to screen therapeutic molecules active as cytoprotectors (an inhibitor of ANT/Vpr interaction) or active as cytotoxics (analogs of Vpr with respect to interaction with ANT and/or VDAC). In this regard, the inventors have established a new ELISA screening test for Vpr ligands and molecules than can inhibit the attachment of ANT to Vpr.

Consequently, one of the objectives of the present invention concerns peptide or non-peptide molecules that can imitate Vpr by attaching themselves to ANT in the cells (or certain cells) of an individual; specifically, a person afflicted with cancer.

The invention also concerns structural or functional inhibitors effective in blocking Vpr/ANT interaction or Vpr/VDAC interaction and thus 1) that inhibit in vitro or in vivo infection by HIV and 2) that inhibit the cytotoxic effect of any ANT ligand (natural, endogenous, xenobiotic) and thus produce a cytoprotective effect in patients afflicted with a disease associated with excess apoptosis.

Thus, the present invention also covers components that can modify the interaction between, on the one hand, Vpr (found in the cells, extracellular fluids, or HIV particles of an individual infected by a retrovirus) or an analog (endogenous [e.g., Bcl-2 or a sub-region of this protein] or xenobiotic) of Vpr and, on the other hand, at least one of the isoforms of ANT found in cells at the mitochondrial membrane level. Molecules derived from ANT or from an interaction pattern (for example, ANT104-116) with Vpr are also considered as active molecules forming a part of the present invention.

The invention also concerns the use of the compounds and inhibitors defined earlier as active principles of pharmaceutical compounds. One possible specific application might be the coupling of Vpr, from a Vpr pattern (e.g., pattern 52-96, 71-82, or 71-96) or from an analog of Vpr, with a molecule that can screen a tumor in vivo. Thus, the invention includes the use of a Vpr pattern (for example, pattern 52-96, 71-82, or 71-96).

The invention also includes the means to screen molecules that can imitate the cytotoxic and/or mitochondrial effect of Vpr (particularly its interaction with ANT and/or VDAC) and the means to screen molecules (cytoprotective) that can modify the interaction between, on the one hand, Vpr (found in the cells, extra-cellular fluids, or HIV particles of individuals infected by a retrovirus) or an analog (endogenous or xenobiotic) of Vpr and, on the other hand, at least one of the isoforms of ANT found in the cell at the mitochondrial membrane level.

Thus, the invention includes the methods to screen agonists (structural or functional analogs of Vpr) or antagonists (inhibitors of Vpr/ANT interaction, or the adoption of a "lethal pore" conformation in response to Vpr, or a structural or functional analog of Vpr) of ANT. Hence, the invention includes at least two screening tests:

a binding test of ANT (or an ANT derived peptide containing, for example, the pattern 104-116 of ANT) on Vpr (or a peptide derived from Vpr containing, for example, the pattern 71-82). The protocol of this test has already been established in the case of binding Vpr 52-96 at the bottom of a plate with 96 wells and to which an ANT or a peptide of ANT containing the pattern 104-116 is attached and then exposed.

a test called a "double test" functional for ANT and that simultaneously evaluates the specific antiport function and the non-specific lethal pore function of ANT. The principle of this test and the detailed protocol are described in Example 5.

A. Plasma surface resonance sensorgrams of the interaction of ANT with Vpr52-96, Vpr52-96[R73A,80A] or an irrelevant control (Co). Only the sensorgram of the interaction with Vpr52-96 exhibits an increase of binding as a function of time and a positive signal at the start of the dissociation phase (off). The calculated $K_D$ ($K_D=k_{on}/k_{off}$) of the interaction is 9.7±6.4 nM (X±SD, n=5).

B. Langmuir isotherm determined at different concentrations of ANT on sensorgrams corrected by subtraction of the blank (sensorgrams obtained with Vpr52-96[R73A,80A]).

C. Modulation of the Vpr52-96-ANT interaction by ANT ligands and ANT-derived peptides. Measurements were performed as in A, in the absence (Ø) or presence of bongkrekic acid (BA, 250 µM), atractyloside (Atr, 50 µM), the ANT104-116 peptide, or three control peptides (all at 5 µM). ANT-2-derived peptide ANT104-116 [DKRTQFWRYFAGN] (SEQ ID NO:3) and control peptides (Co. I: scrambled ANT104-116 [FQNYWGHKRFRDA] (SEQ ID NO:4); Co. II: mutated ANT104-116 [DGHKQFWGYFAGN] (SEQ ID NO:5); Co. III: topologically equivalent peptide (aa 149-161) from the ANT-related human phosphate carrier protein [SNMLGEENTYLWR] (SEQ ID NO:6). Activation or inhibition was calculated as (1-$k_{0a}/k_0$)×100, in which $k_{0a}$ and $k_0$ are the initial velocity in the presence or absence of the agent, respectively.

D. Langmuir isotherm for the binding of ANT104-116 to biotinylated Vpr52-96 (as determined in A). The calculated $K_D$ of the interaction is 35 µM.

E. Schematic diagram showing the topology of ANT and the sequence of the ANT-2-derived peptide ANT104-116 (SEQ ID NO:3).

FIG. 2 presents physical (A, B) and functional (C) interaction between Vpr and liposomes containing ANT.

A. Dose-response curve of FITC-labeled Vpr52-96 binding onto ANT-liposomes and plain liposomes.

B. Binding of FITC-Vpr52-96 (2 µM) to plain liposomes, ANT-proteoliposomes, in the presence or absence of BA (50 µM).

C. Permeabilization of ANT proteoliposomes by Vpr (X±SD, n=3). Liposomes were loaded with 4-methylumbelliferylphosphate (4-MUP) and exposed for 60 min to Atr (200 µM) or the indicated Vpr-derived peptides (1 µM), in the presence or absence of BA (50 µM), ADP (800 µM), and/or the indicated peptides (same as in B, 0.5 μM, pre-incubated with Vpr52-96 for 5 min). Then, alkaline phosphatase was added to convert liposome-released 4-MUP into the fluorochrome 4-methylumbelliferone (4-MU) and the percentage of 4-MUP release induced by Vpr-derived peptides was calculated as described in Material and Methods".

Figure 3B:
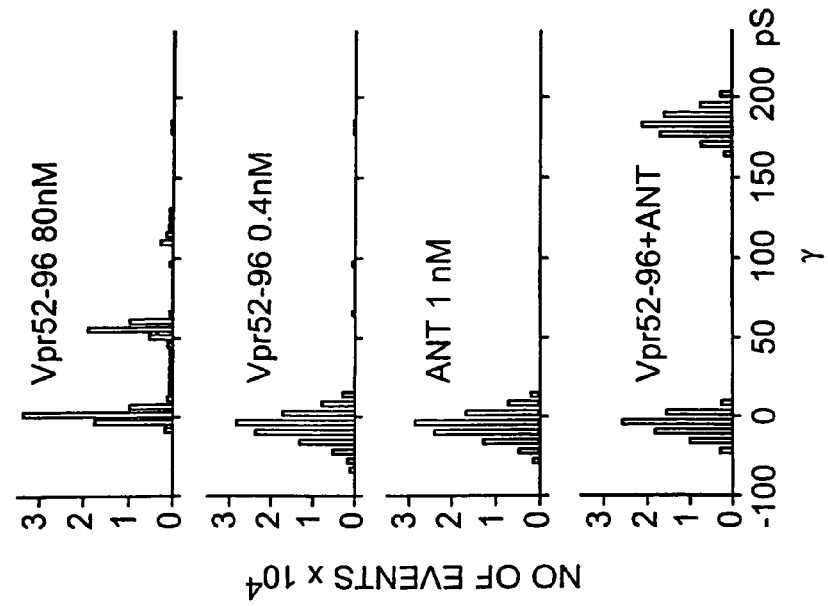
Figure 3A:
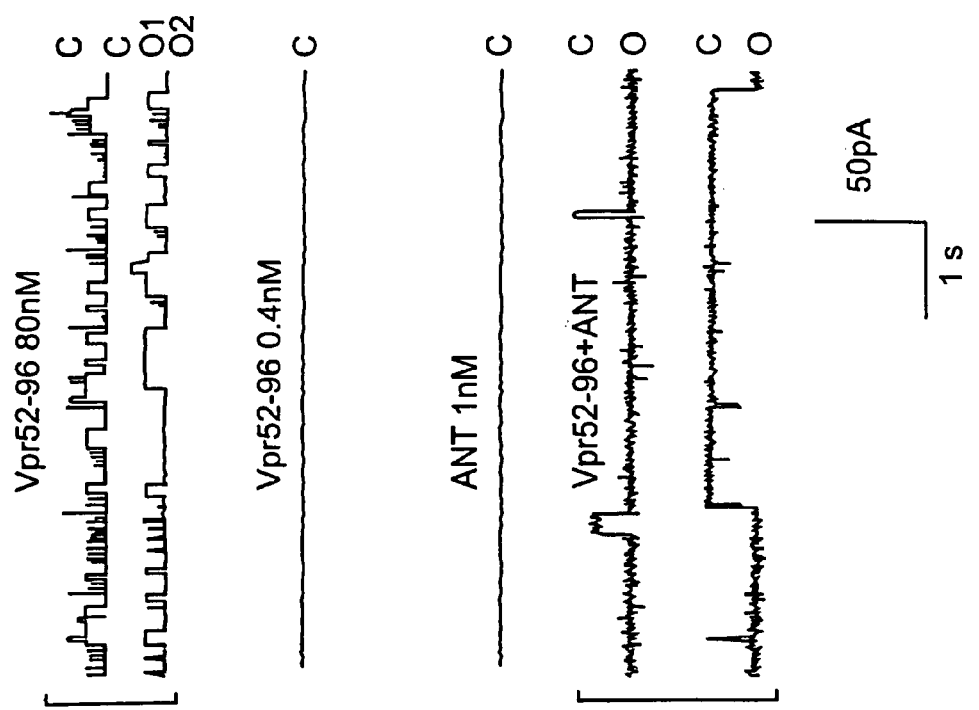

FIG. 3 presents electrophysiological properties of Vpr52-96 and ANT in planar lipid bilayers. Current fluctuations of Vpr52-96 (80 nM, +150 mV), Vpr52-96 (0.4 nM, +100 mV), ANT (1 nM, +110 mV) and Vpr52-96+ANT (0.4:1 nM, +115 mV) and associated histograms (right) of conductance levels are shown.

A. Cooperative effect between ANT and Vpr52-96 at the single channel level. Current fluctuations of Vpr52-96 (80 nM, +150 mV), Vpr52-96 (0.4 nM, +100 mV), ANT (1 nM, +110 mV) and Vpr52-96+ANT (0.4:1 nM, +115 mV) after incorporation into synthetic membranes. Single channel recordings were performed using the "Tip-Dip" technique. The recordings shown are representative for at least three independent determinations.

B. Statistical analysis of conductances obtained in A. Results were expressed as current distributions at different voltages. Conductances (γ; in picosiemens, pS) are calculated by division of current by voltage.

FIG. 4 presents oxidative properties of purified mitochondria exposed to Vpr.

A. Oxygen consumption curves after addition of the indicated agents. Trace a: control mitochondria (no pretreatment). Trace b: mitochondria pretreated for 10 min with 1 μM Vpr52-96. Numbers along the traces are nmol of $O_2$ consumed $min^{-1}$ $mg^{-1}$ protein.

B. Respiratory control (RC) values calculated by dividing oxygen consumption in the presence of CCCP by that measured with oligomycin (determined as in A), 10 min after addition of 1 μM of Vpr-derived peptides (mean values of 3 determinations).

FIG. 5 presents inner versus outer mitochondrial membrane permeabilization.

A. Respirometry performed after addition of NADH and Vpr52-96 (1 μM). Numbers along the traces are nmol of $O_2$ consumed $min^{-1}$ $mg^{-1}$ protein. Note that the Vpr-stimulated, NADH-dependent $0_2$ consumption was fully sensitive to rotenone.

B. Kinetics of Vpr52-96-induced inner membrane permeabilization to NADH and outer membrane permeabilization to reduced cytochrome c. Oxygen consumption was determined in the presence of 2 mM NADH (full squares) as in A (traces C-D) and cytochrome c (15 μM) oxidation (open circles) was spectrofluorometrically measured, as described (Rustin et al., 1994). The 100% value of cytochrome c oxidation was determined by addition of 2.5 mM laurylmaltoside.

C. Kinetics of Vpr52-96-induced $\Delta\Psi_m$ loss and cytochrome c release. Purified mitochondria were treated with 1 μM Vpr52-96 subjected to cytofluorometric determination of the percentage of mitochondria having a low $\Delta\Psi_m$ using the $\Delta\Psi_m$-sensitive fluorochrome JC-1. In parallel, cytochrome c was immunodetected in the supernatant of mitochondria.

FIG. 6 presents Bcl-2-mediated inhibition of Vpr effects on mitochondria.

A. Vpr52-96-induced $\Delta\Psi_m$ dissipation induced in intact cells. COS cells were microinjected with recombinant human Bcl-2 (10 μM), Königs polyanion (PA10, 2 μM), or PBS only, then incubated in the absence (Co.) or presence of 1 μM Vpr52-96 for 3 hours, and stained with the $\Delta\Psi_m$-sensitive dye JC-1 (2 μM; red fluorescence of mitochondria with a high $\Delta\Psi_m$, green fluorescence of mitochondria with a low $\Delta\Psi_m$).

B. Effect of Bcl-2 on the Vpr-induced inner MMP to NADH. Mitochondria were left untreated (Co.) or pretreated (10 min) with Bcl-2 (0.8 μM) or BA (10 μM). Oxygen consumption of purified mitochondria was measured as in FIG. 5 after addition of succinate+CCCP or NADH, as indicated.

C. Ultrastructural effects of Vpr on isolated mitochondria. Electron micrographs were obtained after incubation of mitochondria for 5 or 15 min with 3 μM Vpr52-96, after pre-incubation (5 min) with 0.8 μM Bcl-2 or 2 μM PA10.

D. Effect of Bcl-2 and PA-10 on Vpr52-96-induced $\Delta\Psi_m$ dissipation in purified mitochondria. Isolated mitochondria (200 μg protein per ml) were pre-incubated with the indicated inhibitors (5 μM CsA, 50 μM BA, 0.8 μM Bcl-2, 2 μM PA10; 5-10 min), washed (10 min, 6800 g, 20° C.), incubated with the $\Delta\Psi_m$-sensitive dye JC-1 (200 nM, 10 min), exposed to Vpr52-96 (3 μM, 5 min), and subjected to flow cytometric determination of the fluorescence (570-595 nm) and the particle size (FSC). Numbers indicate the percentage of JC-$1^{high}$ and JC-$1^{low}$ mitochondria among ~$10^4$ events.

E. Quantitation of the frequency of JC-$1^{low}$ mitochondria (X±SD, n=5) after incubation with different Vpr-derived peptides. Purified mitochondria were preincubated 10 min with or without Bcl-2 (0.8 μM), Bcl-2Δ$\alpha_{5/6}$ (0.8 μM) or BA (10 μM) in PT buffer, incubated with the $\Delta\Psi_m$-sensitive dye JC-1 (200 nM, 10 min), and then treated 5 min with 3 μM of Vpr52-96 (wt, biotinylated, or modified as indicated), or 10 min. with 5-10 μM of Vpr1-96, Vpr1-51, Vpr71-96, Vpr71-82 (wt or modified as indicated), and finally subjected to flow cytometric analysis as in D.

Figure 7A:
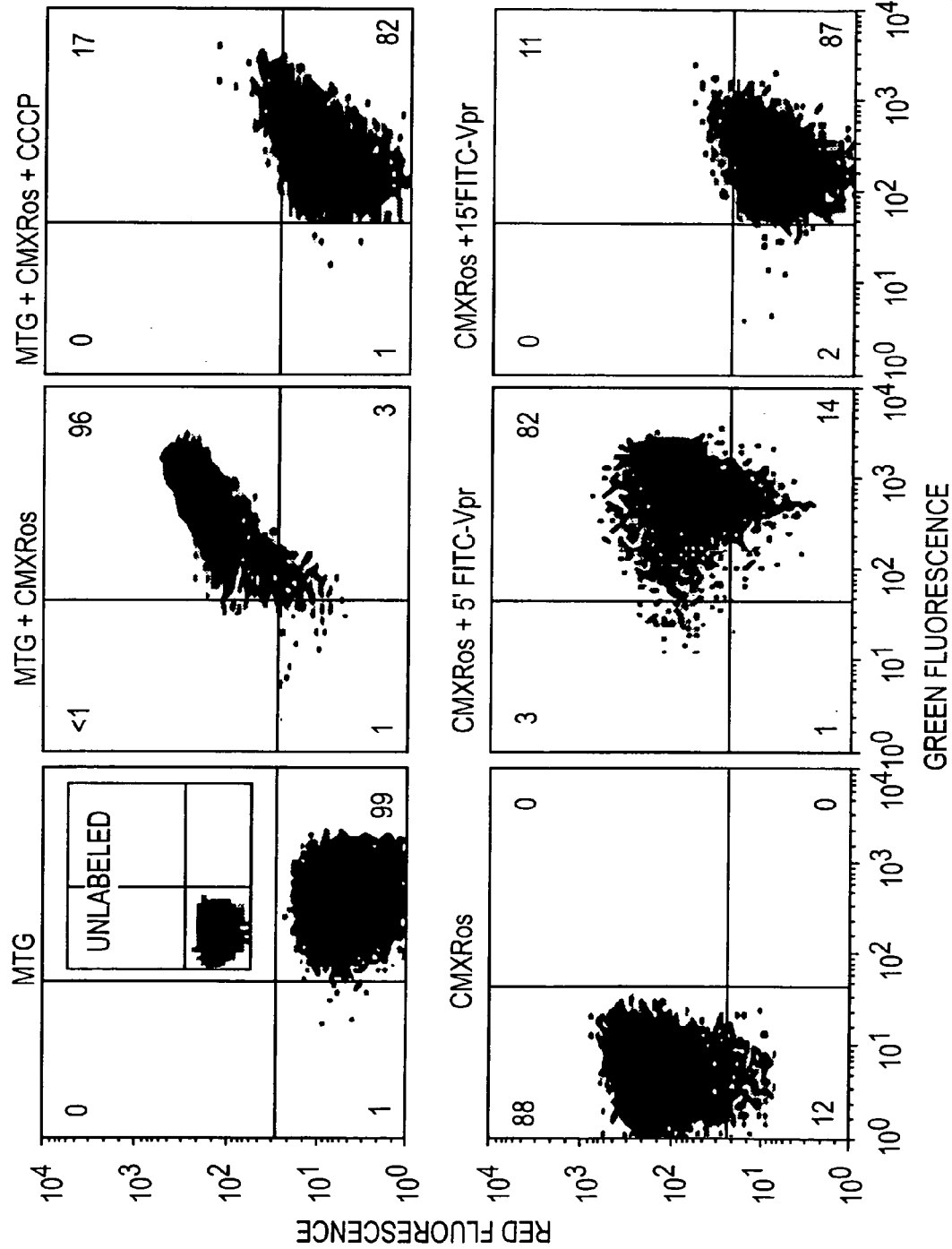

FIG. 7 presents differential effect of Bcl-2 and PA-10 on Vpr52-96 binding to mitochondria.

A. Vpr52-96 binds mitochondria before inducing $\Delta\Psi_m$ loss. Mitochondria were left unstained (insert in Co.) or exposed to the $\Delta\Psi_m$-insensitive mitochondrial dye MitoTracker® Green (75 nM), alone (MTG) or with 0.5 μM of FITC-Vpr52-96; green fluorescence), in combination with the $\Delta\Psi_m$-sensitive mitochondrial dye MitoTracker® Red (CMXRos; red Fluorescence) followed by cytofluorometric two-color analysis. Numbers indicate the percentage of mitochondria in each quadrant.

B. PA-10 but not Bcl-2 inhibit Vpr52-96 binding to mitochondria. Mitochondria were pre-incubated 10 min. with the indicated inhibitors and the percentage of FITC-Vpr52-96-labelled mitochondria is determined as in A. C. Inhibitory effect of Bcl-2 on affinity purification of ANT by biotinylated Vpr52-96. Mitochondria were incubated with the indicated inhibitors, and then exposed for 30 min at RT with 5 μM biotinylated Vpr52-96. Mitochondria were lysed either after incubation with biotinylated Vpr52-96 (upper panel) or lysed before (lower panel) with Tris/HCl as described in materials and methods. Biotinylated Vpr52-96 complexed with its mitochondrial ligands was retained on avidin-agarose and subjected to immunoblot detection of ANT.

Figure 8B:
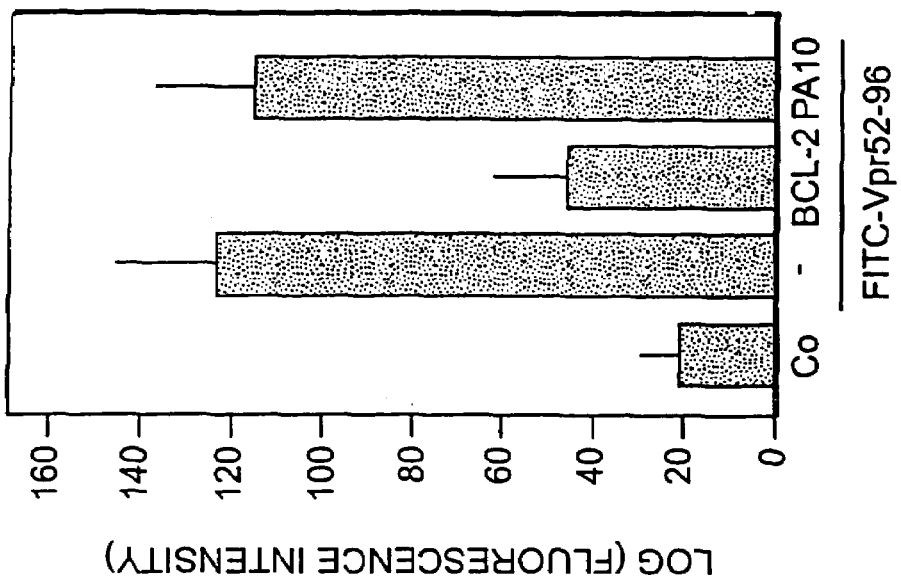
Figure 8A:
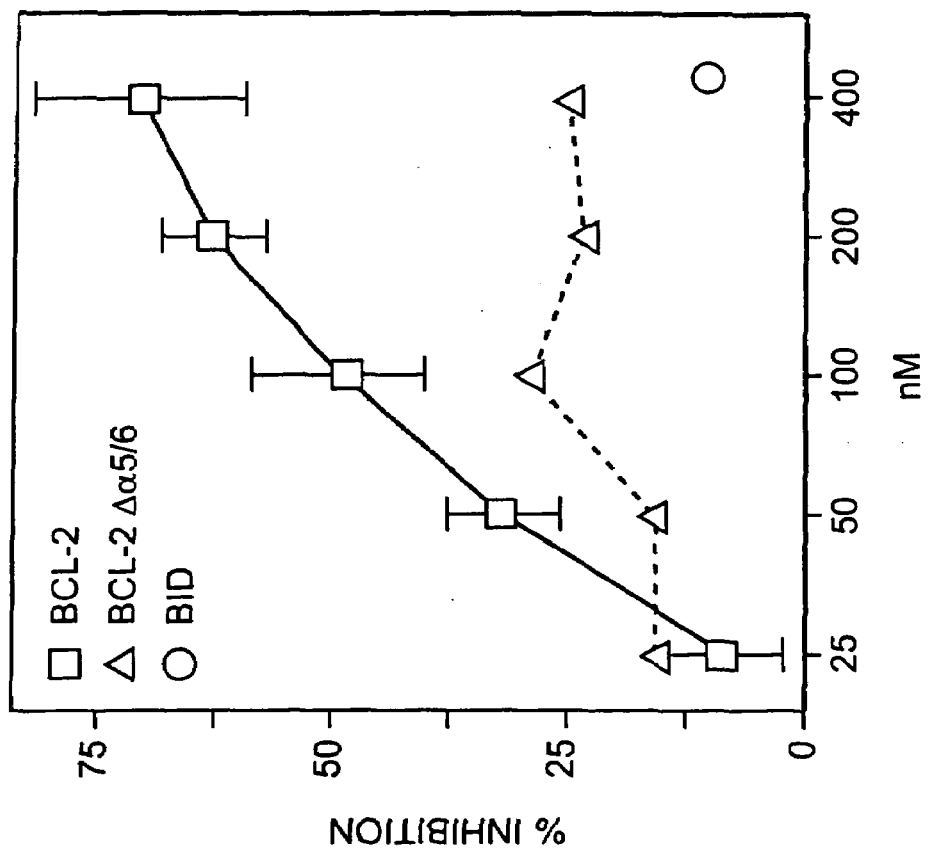

FIG. 8 presents Bcl-2-mediated inhibition of the Vpr-ANT interaction.

A. Plasmon surface resonance determination of the Bcl-2-mediated inhibition of interaction between Vpr52-96 and native purified ANT. The interaction was measured after addition of the indicated concentrations of recombinant Bcl-2, Bcl-2Δ$\alpha_{5/6}$, or recombinant Bid, and data (X±SD, n=3) were calculated as in FIG. 1.

B. Effect of Bcl-2 on Vpr binding to ANT proteoliposomes. The retention (X±SD, n=3) of FITC-labeled Vpr52-96 on ANT proteoliposomes preincubated with 800 nM of Bcl-2 or 2 μM PA10 was assessed as in FIG. 2A. C. Effect of Bcl-2 on the formation of Vpr-ANT channels in planar lipid bilayers. Single channel recordings (+75 mV) of Vpr52-96+ANT+Bax (0.4:1:0.3 nM) and Vpr52-96+ANT+Bcl-2 (0.4:1:1 nM) and corresponding amplitude histograms are displayed. Control values for Vpr52-96+ANT alone are similar as in FIG. 1e (not shown). c, closed; o, open.

Figure 9:
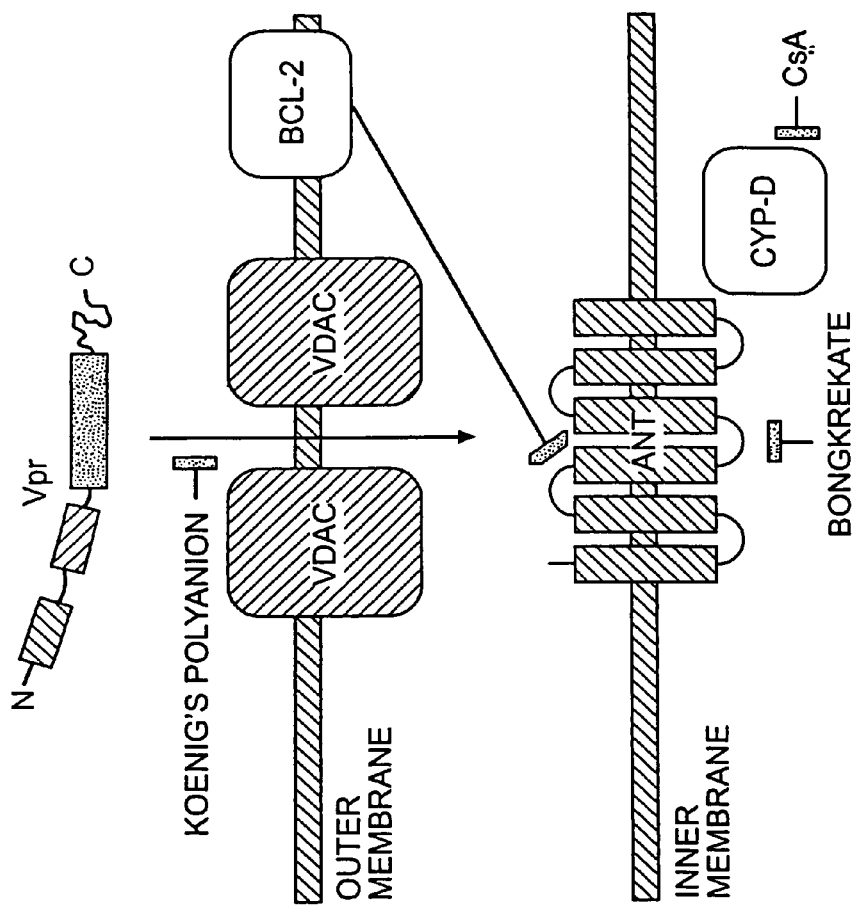

FIG. 9 presents a model of the Vpr/PTPC interactions. Vpr crosses the outer membrane through VDAC, which is inhibited by Koenig's polyanion. Vpr then interacts with ANT. Bcl-2 and the ANT ligand bongkrekate inhibit the binding of Vpr to ANT, whereas CsA indirectly affects the pore forming function of ANT via its effect on cyclophilin D (Cyp-D).

DETAILED DESCRIPTION OF THE INVENTION

The invention relates to discovery that the proapoptotic HIV-1-encoded protein Vpr induces mitochondrial membrane permeabilization via its physical and functional interaction with the mitochondrial inner membrane protein ANT (adenine nucleotide translocator, also called ADP/ATP carrier). This is shown using a variety of different techniques: surface plasmon resonance, electrophysiology, synthetic proteoliposomes, studies on purified mitochondria (respirometry, electron microscopy, organellofluorometry), as well as microinjection of intact cells. The mode of action of Bcl-2 acts on ANT and to prevent Vpr-mediated mitochondrial effects.

This invention relates to the discovery that Vpr primarily affects IM and not OM permeability in vitro. Vpr binds ANT in an ANT conformation-dependent fashion (FIGS. 1 and 2) and cooperates with ANT to form channels (FIG. 3) which permeabilize IM before OM becomes permeable to cytochrome c (FIGS. 4 and 5). Bcl-2 antagonizes this effect, based on two independent observations. First, its mode of action clearly differs from that of the VDAC inhibitor PA10 (FIGS. 6 and 7). Second, Bcl-2 can affect the physical and functional ANT-Vpr interaction in a synthetic, VDAC-free system (FIG. 8). Although these data do not exclude the possibility that Bcl-2 and other members of Bcl-1 family modulate the permeability of VDAC to relatively large, globular proteins (14.5 kDa for cytochrome c, as opposed to the linear, mostly α helical structure of Vpr52-96 resolved by NMR, W. Schüler, et al., *J. Mol. Biol.* 285, 2105-2117 (1999)), they indicate that, at least in this particular model, Bcl-2 exerts its membrane-protective mitochondrial effect via ANT.

HIV-1 Viral protein R (Vpr) interacts with the permeability transition pore complex (PTPC) to trigger mitochondrial membrane permeabilization (MMP) and consequent apoptosis. Vpr binds to the adenine nucleotide translocator (ANT), an inner mitochondrial membrane protein. E. Jacotot, et al., *J. Exp. Med.* 191, 3345 (2000). When Vpr binds to ANT, it cooperatively forms large conductance channels in synthetic membranes. When added to purified mitochondria, Vpr uncouples the respiratory chain and induces a rapid inner MMP which precedes outer MMP to cytochrome c, Vpr-induced matrix swelling and inner MMP to protons and NADH are prevented by preincubation of purified mitochondria with recombinant Bcl-2 protein. In contrast to König's polyanion, a specific inhibitor of the voltage-dependent anion channel (VDAC), Bcl-2 fails to prevent Vpr from crossing the outer mitochondrial membrane. Bcl-2 reduces the ANT-Vpr interaction and abolishes channel formation by the ANT-Vpr complex. Hence, both Vpr and Bcl-2 modulate MMP through a direct interaction with ANT.

Methods of Altering or Preventing Binding of Vpr to ANT

The discovery of the physical and functional interaction of Vpr with ANT enables methods of altering or preventing binding of Vpr to ANT. As illustrated in Examples 1-4, the interaction of Vpr to ANT can be detected and modulated in a variety of different assay systems. For example, Bcl-2 modulates the physical and functional interaction of Vpr with ANT. Likewise, a peptide, ANT104-116, corresponding to the overlap between the Bcl-2 binding motif and the second ANT loop inhibits ANT-Vpr binding. Thus, these molecules can be used to alter or prevent binding of Vpr to ANT. Other peptidic or non-peptidic molecules can be designed to similarly inhibit this binding.

The identification of Vpr-ANT binding allows the generation of molecules that can modulate apoptosis. The methods presented in the Examples, and other conventional techniques, can be adapted to screen for Vpr, Bcl-2, or ANT variants, or other polypeptides or molecules that affect Vpr-ANT binding. This allows for the generation of molecules capable of enhancing or inhibiting Vpr-ANT binding. The activity of these molecules can be assessed by competitive binding assays. For example, molecules can be assessed for there ability to inhibit ANT-Vpr binding using the binding assays described in the Examples. The skilled artisan understands that many other techniques could similarly be used. The identified molecules can be further assessed for apoptotic activity by conventional techniques. Furthermore, based on the structure of Vpr molecules determined to bind to ANT, structurally similar molecules can be designed to mimic Vpr activity or to inhibit this activity.

In one embodiment, soluble versions of Vpr or ANT polypeptides can be incubated with cells to enhance or inhibit the induction of apoptosis. In one embodiment these polypeptides contain mutations that interfere with apoptosis. In another embodiment, these polypeptides contain mutations that enhance apoptosis. In one embodiment, these polypeptides are synthetic. In another embodiment, these polypeptides are produced by recombinant techniques.

Vpr and ANT polypeptides and peptides of greater than 9 amino acids that inhibit or augment Vpr-ANT binding, mitochondrial membrane permeabilization, or apoptosis are an embodiment of the invention, as well as peptides that are at least 10-20, 20-30, 30-50, 50-100, and 100-365 amino acids in size. DNA fragments encoding these polypeptides and peptides are encompassed by the invention.

Synthetic polypeptides and peptides can be generated by a variety of conventional techniques. Such techniques include those described in B. Merrifield, *Methods Enzymol.* 289:3-13, 1997; H. Ball and P. Mascagni, *Int. J. Pept. Protein Res.* 48:31-47, 1996; F. Molina et al., *Pept. Res.* 9:151-155, 1996; J. Fox, *Mol. Biotechnol.* 3:249-258, 1995; and P. Lepage et al., *Anal. Biochem.* 213: 40-48, 1993.

In another embodiment, peptides can be prepared by subcloning a DNA sequence encoding a desired peptide sequence into an expression vector for the production of the desired peptide. The DNA sequence encoding the peptide is advantageously fused to a sequence encoding a suitable leader or signal peptide. Alternatively, the DNA fragment may be chemically synthesized using conventional techniques. The DNA fragment can also be produced by restriction endonuclease digestion of a clone of, for example HIV-1, DNA using known restriction enzymes (New England Biolabs 1997 Catalog, Stratagene 1997 Catalog, Promega 1997 Catalog) and isolated by conventional means, such as by agarose gel electrophoresis.

In another embodiment, the well known polymerase chain reaction (PCR) procedure can be employed to isolate and amplify a DNA sequence encoding the desired protein fragment. Oligonucleotides that define the desired termini of the DNA fragment are employed as 5' and 3' primers. The oligonucleotides can contain recognition sites for restriction endonucleases, to facilitate insertion of the amplified DNA fragments into an expression vector. PCR techniques are described in Saiki et al., *Science* 239:487 (1988); *Recombinant DNA Methology*, Wu et al., eds., Academic Press, Inc., San Diego (1989), pp. 189-196; and *PCR Protocols: A Guide to Methods and Applications*, Innis et al., eds., Academic Press, Inc., (1990). It is understood of course that many techniques could be used to prepare polypeptide and DNA fragments, and that this embodiment in no way limits the scope of the invention.

Screening Methods with Vpr and ANT

Vpr or ANT polypeptides can be assessed for their ability to mediate apoptosis, as well as to block Vpr mediated apoptosis. For example, fragments of Vpr can be assessed for their ability to block native Vpr binding to ANT by conventional titration experiments.

In one embodiment, surface plasmon resonance is used to assess binding of Vpr to ANT as described herein. In another embodiment, electrophysiology is used to assess binding of Vpr to ANT as described herein. In another embodiment, purified mitochondria are used to assess binding of Vpr to ANT as described herein. In another embodiment, synthetic proteoliposomes are used to assess binding of Vpr to ANT as described herein. In another embodiment, microinjection of live cells is used to assess binding of Vpr to ANT as described herein. It is understood of course that many techniques could be used to assess binding of Vpr to ANT, and that these embodiments in no way limit the scope of the invention.

In another embodiment, the yeast two-hybrid system developed at SUNY (described in U.S. Pat. No. 5,283,173 to Fields et al.; J. Luban and S. Goff., *Curr Opin. Biotechnol.* 6:59-64, 1995; R. Brachmann and J. Boeke, *Curr Opin. Biotechnol.* 8:561-568, 1997; R. Brent and R. Finley, *Ann. Rev. Genet.* 31:663-704, 1997; P. Bartel and S. Fields, *Methods Enzymol.* 254:241-263, 1995) can be used to screen for a inhibitors of the Vpr-ANT interaction as follows. Vpr, or portions thereof responsible for interaction, can be fused to the Gal4 DNA binding domain and introduced, together with an ANT molecule fused to the Gal 4 transcriptional activation domain, into a strain that depends on Gal4 activity for growth on plates lacking histidine. Interaction of the Vpr polypeptide with an ANT molecule allows growth of the yeast containing both molecules and allows screening for the molecules that inhibit or alter this interaction (i.e., by inhibiting or augmenting growth).

In an alternative embodiment, a detectable marker (e.g. β-galactosidase) can be used to measure binding in a yeast two-hybrid assay.

In addition, the identification of Vpr as an ANT-binding molecule allows methods of detecting and quantifying ANT expression in cells. For example, by contacting a labeled Vpr polypeptide with a biological sample comprising ANT and detecting the Vpr-ANT complex, the level of ANT can be determined.

Purified ANT polypeptides (including proteins, polypeptides, fragments, variants, oligomers, and other forms) may be tested for the ability to bind Vpr in any suitable assay, such as a conventional binding assay. Similarly, Vpr polypeptides (including proteins, polypeptides, fragments, variants, oligomers, and other forms) may be tested for the ability to bind ANT. To illustrate, the Vpr polypeptide may be labeled with a detectable reagent (e.g., a radionucleotide, chromophore, enzyme that catalyzes a colorimetric or fluorometric reaction, and the like). The labeled polypeptide is contacted with cells expressing ANT. The cells then are washed to remove unbound labeled polypeptide, and the presence of cell-bound label is determined by a suitable technique, chosen according to the nature of the label.

Alternatively, the binding properties of Vpr polypeptides and polypeptide fragments can be determined by analyzing the binding of Vpr polypeptides and polypeptide fragments to ANT-expressing cells by FACS analysis and/or immunofluorescence. This allows the characterization of the binding of Vpr and ANT polypeptides and polypeptide fragments, and the discrimination of relative abilities of Vpr polypeptides and polypeptide fragments to bind to ANT. In vitro binding assays with Vpr and ANT can similarly be used to characterize Vpr-ANT binding activity.

Another type of suitable binding assay is a competitive binding assay. To illustrate, biological activity of a variant may be determined by assaying for the variant's ability to compete with the native protein for binding to Vpr or ANT.

Competitive binding assays can be performed by conventional methodology. Reagents that may be employed in competitive binding assays include radiolabeled Vpr and intact cells expressing ANT (endogenous or recombinant). For example, a radiolabeled Vpr fragment can be used to compete with a soluble Vpr variant for binding to ANT in cells. Instead of intact cells, one could substitute ANT protein bound to a solid phase.

Another type of competitive binding assay utilizes radiolabeled Vpr and isolated mitochondria. Qualitative results can be obtained by competitive autoradiographic plate binding assays, while Scatchard plots (Scatchard, *Ann. N.Y. Acad. Sci.* 51:660, 1949) may be utilized to generate quantitative results.

Peptidic or Non-Peptidic Molecules that Affect Interaction of Vpr to ANT or Mimic its Capacity to Interact with ANT Variants The invention encompasses variants of Vpr or ANT that are altered in their binding activity. Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants may also bind with increased affinity. In one embodiment, a variant is an agonist of the native Vpr for ANT's biological activity. In another embodiment, a variant is an antagonist of the native Vpr for ANT's biological activity. Agonistic or antagonistic activity can be readily determined by the procedures described herein.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known. Variants can be generated using conventional techniques including random or site-directed mutagenesis.

Antibodies

Within an aspect of the invention, Vpr and ANT polypeptides, and peptides based on the amino acid sequence of Vpr and ANT, can be utilized to prepare antibodies that specifically bind to Vpr and ANT polypeptides. Antibodies that are immunoreactive with the polypeptides of the invention are provided herein. In this aspect of the invention, the polypeptides based on the amino acid sequence of Vpr and ANT can be utilized to prepare antibodies that specifically bind to Vpr and ANT. Such antibodies specifically bind to the polypeptides via the antigen-binding sites of the antibody (as opposed to non-specific binding). Thus, the polypeptides, fragments, variants, fusion proteins, etc., as set forth above may be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques as described below.

The term "antibodies" is meant to include polyclonal antibodies, monoclonal antibodies, fragments thereof, particularly antigen binding fragments such as F(ab')2 and Fab fragments, as well as any recombinantly produced binding partners. Antibodies are defined to be specifically binding if they bind with a $K_a$ of greater than or equal to about $10^7 M^{-1}$. Affinities of binding partners or antibodies can be readily determined using conventional techniques, for example those described by Scatchard et al., *Ann. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well known in the art. In general, purified Vpr (or ANT) or a peptide based on the amino acid sequence of Vpr (or ANT) that is appropriately conjugated is administered to the host animal typically through parenteral injection. The immunogenicity of Vpr (or ANT) can be enhanced through the use of an adjuvant, for example, Freund's complete or incomplete adjuvant. Following booster immunizations, small samples of serum are collected and tested for reactivity to Vpr or ANT polypeptide. Examples of various assays useful for such determination include those described in *Antibodies: A Laboratory Manual*, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice, are injected intraperitoneally at least once and preferably at least twice at about 3 week intervals with isolated and purified Vpr (or ANT), conjugated Vpr (or ANT) peptide, optionally in the presence of adjuvant. Mouse sera are then assayed by conventional dot blot technique or antibody capture (ABC) to determine which animal is best to fuse. Approximately two to three weeks later, the mice are given an intravenous boost of Vpr (or ANT) or conjugated Vpr (or ANT) peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as $^{125}$I-Vpr (or $^{125}$I-ANT), is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al.

(*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Once isolated and purified, the antibodies against Vpr and ANT, and other Vpr and ANT binding proteins, can be used to detect the presence of Vpr and ANT in a sample using established assay protocols. Further, the antibodies of the invention can be used therapeutically to bind to Vpr or ANT and inhibit its activity in vivo.

Antibodies directed against Vpr or ANT and other Vpr or ANT binding proteins can be used to modulate the biological activity of Vpr and ANT. One class of these antibodies produce mitochondrial membrane permeabilization and apoptosis. In contrast, another class of these antibodies can inhibit mitochondrial membrane permeabilization and apoptosis.

Those antibodies that additionally can block Vpr-ANT binding of may be used to inhibit a biological activity that results from such binding. Such blocking antibodies may be identified using any suitable assay procedure, such as by testing antibodies for the ability to inhibit binding of Vpr to ANT. Alternatively, blocking antibodies may be identified in assays for the ability to inhibit a biological effect that results from binding of Vpr to ANT in cells.

Such an antibody may be employed in an in vitro procedure, or administered in vivo to inhibit a biological activity mediated by the entity that generated the antibody. Disorders caused or exacerbated (directly or indirectly) by the interaction of Vrp with ANT. A therapeutic method involves in vivo administration of a blocking antibody to a mammal in an amount effective in inhibiting ANT-mediated apoptosis. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to ANT, induce biological effects (e.g., apoptosis) similar to the biological effects induced when Vpr binds to ANT. Agonistic antibodies may be used to induce ANT-mediated apoptosis of cells.

Compositions comprising an antibody that is directed against Vpr or ANT, and a physiologically acceptable diluent, excipient, or carrier, are provided herein. Suitable components of such compositions are as described above for compositions containing Vpr or ANT.

Also provided herein are conjugates comprising a detectable (e.g., diagnostic) or therapeutic agent, attached to the antibody. Examples of such agents are presented above. The conjugates find use in in vitro or in vivo procedures.

Other Molecules

The invention also encompasses molecules that compete for or enhance the binding of Vpr to ANT, which can be identified through the screening assays described herein or by structure-based design using, for example, molecular modeling of Vpr-ANT binding.

Pharmaceutical and Diagnostic Compositions

Compositions of the present invention may contain a peptidic or non-peptidic molecules in any form, such as native proteins, variants, derivatives, oligomers, and biologically active fragments. In particular embodiments, the composition comprises a soluble polypeptide or an oligomer comprising soluble Vpr, Bcl-2, or ANT polypeptides or fragments.

Compositions comprising an effective amount of a molecule of the present invention, in combination with other components such as a physiologically acceptable diluent, carrier, or excipient, are provided herein. The molecules can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Methods for Screening for ANT Alterations

The invention also provides methods for screening for genetic or epigenetic alterations in the expression or structure of the three ANT isoforms in humans.

The invention provides for diagnosis of diseases associated with aberrant ANT expression. For example, a particular cancer may have a specific modification of ANT associated with it. Diagnosis of that cancer can be achieved by using Vpr or a fragment of Vpr capable of retaining binding to ANT in a binding assay, for example, as described herein. The expression or structure of the three ANT isoforms in patients can thereby be determined and a diagnosis achieved.

Methods for Specific Cell Killing

Vpr, or a biologically active fragment thereof such as vpr52-96, can be used to induce apoptosis in cells. In one embodiment, a vpr52-96 peptide is fused to molecule for targeting to a specific cell type and induces apoptosis in that cell type. In a further embodiment, a Vpr-targeting molecule conjugate specifically kills cancer cells. The methodology can be similar to the successful use of a recombinant chimeric protein containing interleukin 2 (IL-2) protein fused to Bax to selectively kill IL-2 receptor-bearing cells in vitro. R. Aqeilan, S. Yarkoni, and H. Lorberboum-Galski, FEBS Lett. 457:271-6 (1999).

In other embodiments, biologically active Vpr-targeting molecule conjugates can be used to specifically target and kill other cell types involved in disease.

Double Test

To study ANT's role in apoptosis and, more specifically, ANT's role in the permeabilization of mitochondrial membranes (Brenner et al., Oncogene, 2000; Costantini at al., Oncogene, 2000), the inventors have developed a functional double test that makes it possible to measure simultaneously the antiport (vital) function and the pore (lethal) function of ANT in artificial lipid double-layers or liposomes.

The principle of the functional double test is based on the reconstitution of ANT in liposomes, the encapsulation of different substrates (fluorescent substrate and ATP) in the interior of proteoliposomes, the addition of enzymes and ADP to the exterior of the liposomes, and then measurement by fluorescence of the salting out of a substrate through the pore formed by ANT and, at the same time, the measurement by luminescence of ATP translocated in response to exogenous ADP. Any peptide or non-peptide compound can be reconstituted with ANT during the formation of liposomes (e.g., Bax, Bcl-2, Bcl-x(L)), encapsulated in liposomes or added in an external manner to proteoliposomes (e.g., addition of peptide molecules [e.g., Vpr, Vpr52-96], Bid, etc.) or not (atractyloside, calcium, t-BHP, diamide, BA, cyclosporine A., verteporfin, etc.) to determine its impact on the two functions of ANT. Quantitative measurements can be performed in a fixed point or kinetic manner. This test is operation in 96 well microplates and can be adapted to HTS (high throughput screening).

This functional double test enables the screening of molecules that induce or inhibit apoptosis, of ANT partner molecules capable of transforming or of facilitating the ANT-to-pore transformation, or the diagnosis of particular functional forms of ANT (alteration of vital and/or lethal functions, alterations of the ratio of ANT isoforms). The antiport function test makes it possible to evaluate the toxicity of molecules vis-à-vis the vital function of ANT.

The specification is most thoroughly understood in light of the teachings of the references cited within the specification which are hereby incorporated by reference. The embodiments within the specification and the examples provide an illustration of embodiments of the invention and should not be construed to limit the scope of the invention. The skilled artisan readily recognizes that many other embodiments are encompassed by the invention.

EXAMPLE 1

Physical and Functional Interaction Between Vpr and ANT

Figures 1A, 1B:
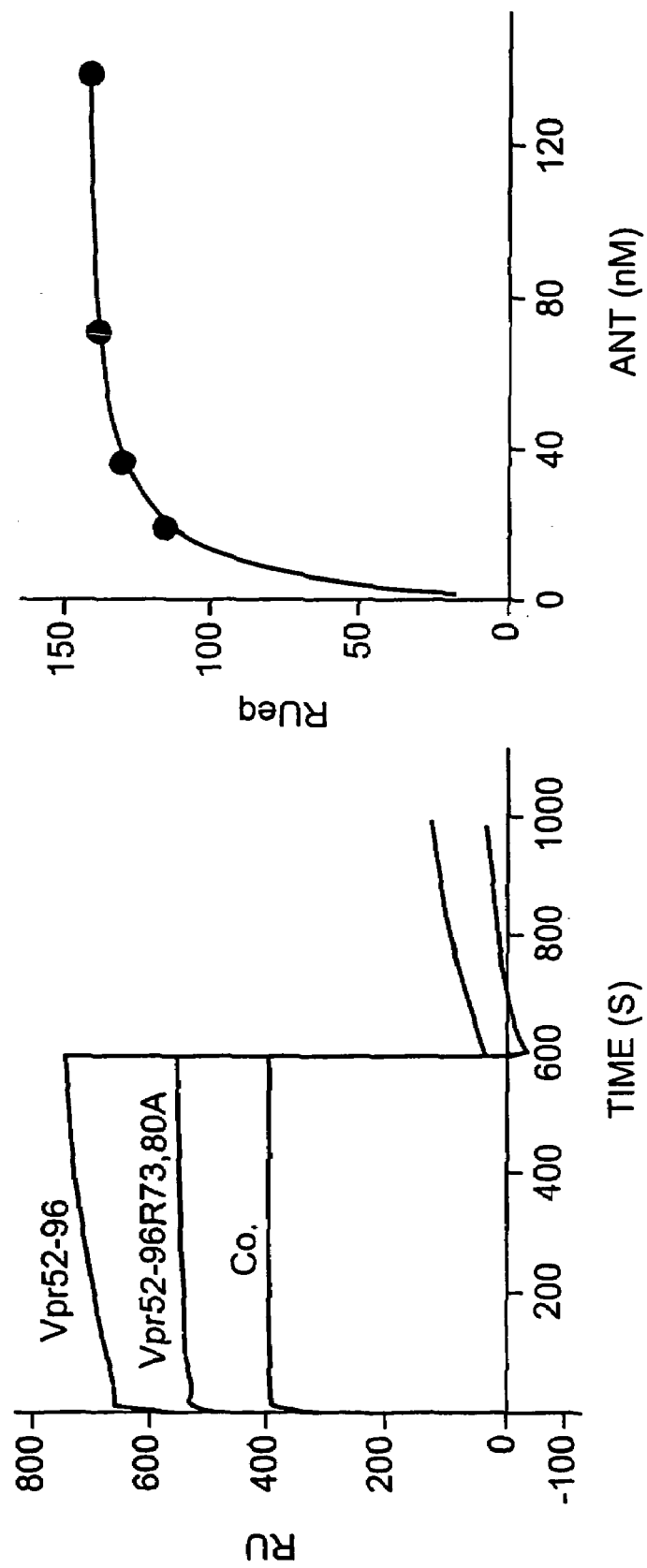
FIG. 1 presents physical and functional interaction between Vpr and ANT.
Figure 1E:
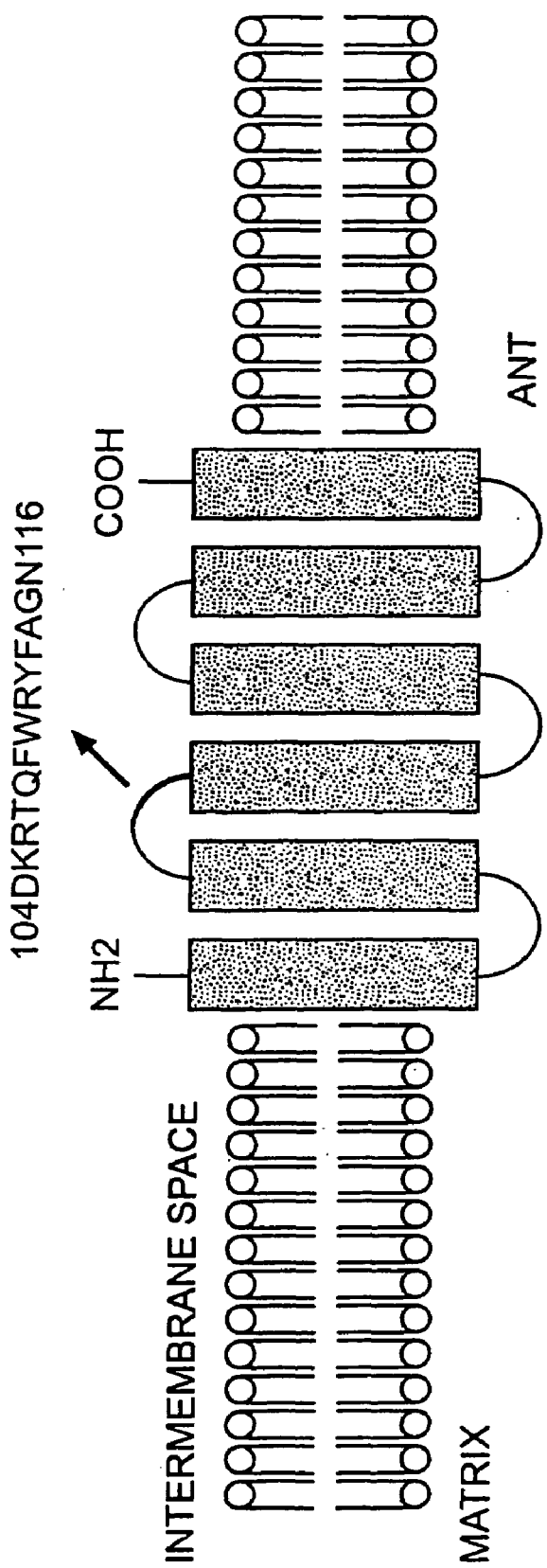
Figure 2B:
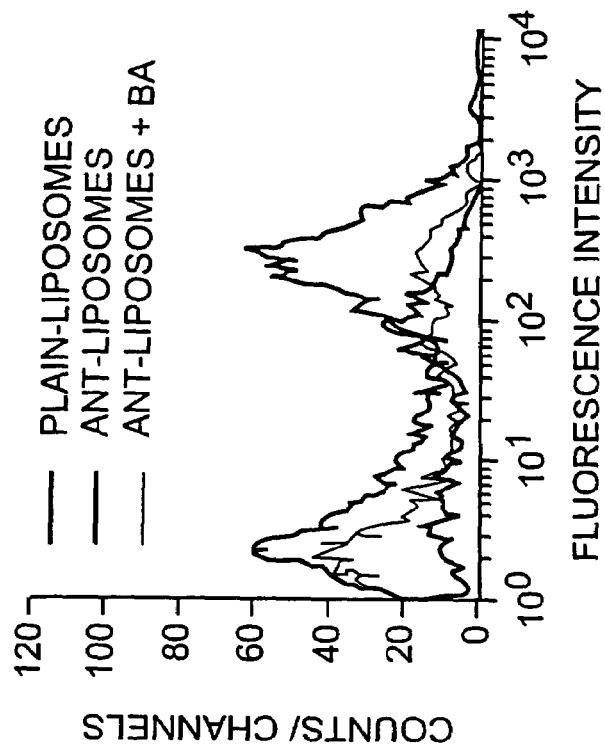
Figure 2A:
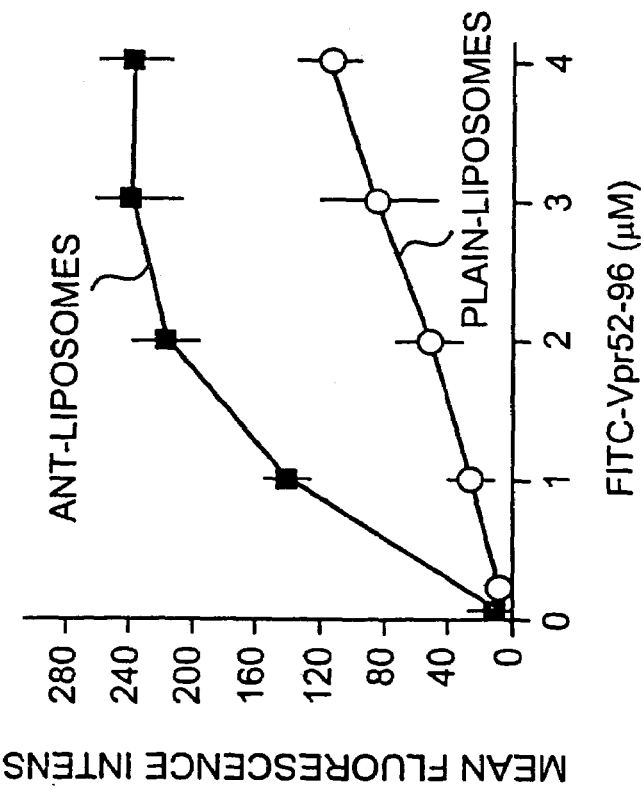
Figure 2C:
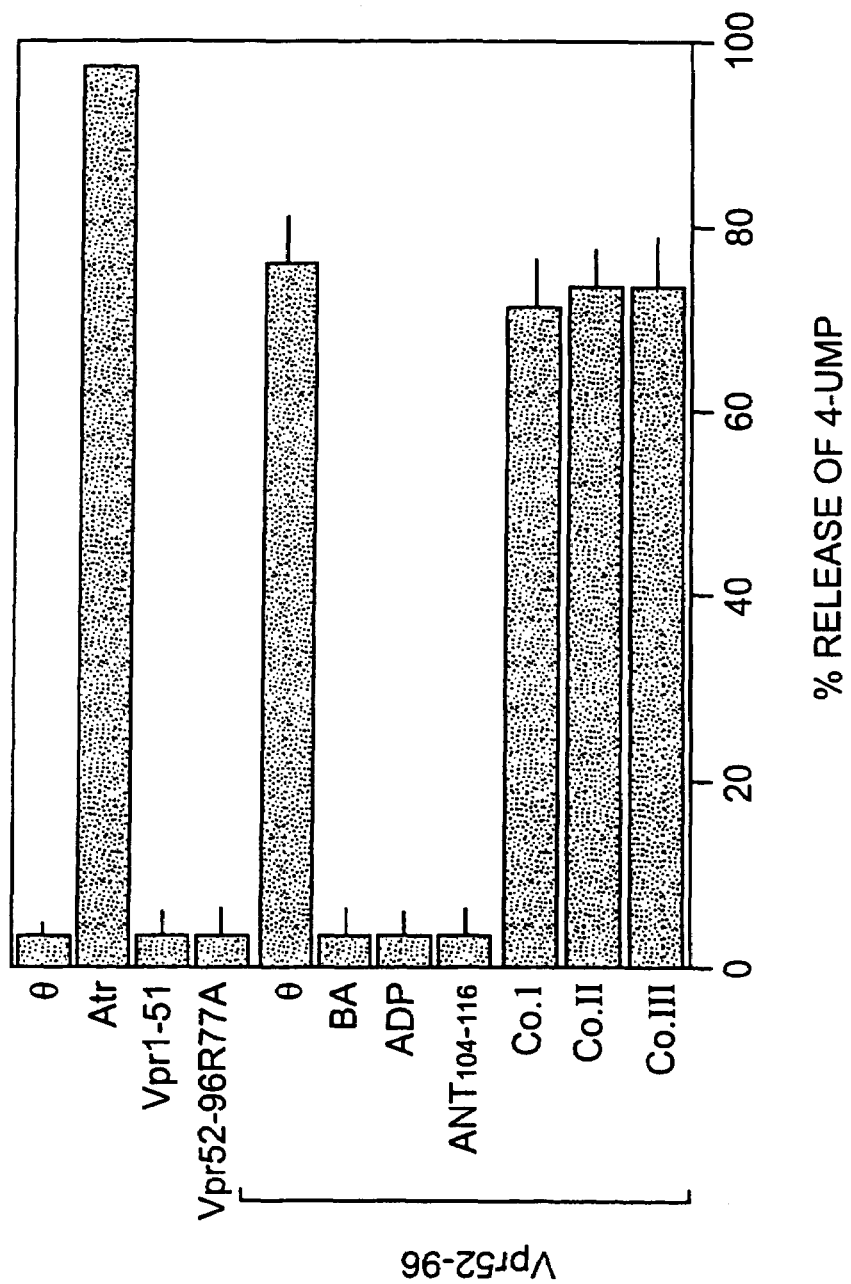

Surface plasmon resonance measurements indicate that purified detergent-solubilized ANT protein binds to the immobilized Vpr C-terminal moiety biotin-Vpr52-96 (but to a far lesser extent to mutated biotin-Vpr52-96[R73,80A]) with an affinity in the nanomolar range (FIGS. 1A and B). This interaction is modulated by two ANT ligands which differentially affect ANT conformation (M. Klingenberg, *J. Membrane Biol.* 56, 97-105 (1980)), namely the PTPC activator atractyloside (Atr), which favors Vpr binding, and the PTPC inhibitor bongkrekic acid (BA), which reduces Vpr binding (FIG. 1C). Vpr52-96 binding to membranes is greatly facilitated in liposomes in which ANT has been reconstituted as compared to protein-free liposomes (FIG. 2A). This ANT effect is inhibited by BA (FIG. 2B). Vpr52-96 (but not the N-terminal moiety of Vpr [Vpr1-51] nor mutated Vpr52-96, in which arginine 77 is replaced by alanine, Vpr52-96 [R77A]) also causes permeabilization of ANT proteoliposomes (FIG. 2C), yet has no effect on plain liposomes.

Bcl-2-like proteins bind to a motif of ANT (aa 105-155), I. Marzo, et al., *Science* 281, 2027-2031 (1998), whose implication in apoptosis control has been confirmed by deletion mapping of ANT. M. K. A. Bauer, A. Schubert, O. Rocks, S. Grimm, *J. Cell Biol.* 147, 1493-1501 (1999). This motif partially overlaps with the second ANT loop (aa 92-116), a regulatory domain exposed to the intermembrane space. G. Brandolin, A. Le-Saux, V. Trezeguet, G. J. Lauquinn, P. V. Vignais, *J. Bioenerg. Biomembr.* 25, 493-501 (1993). M. Klingenberg, *J. Bioenerg. Biomembr.* 25, 447-457 (1993). A peptide corresponding to the overlap between the Bcl-2 binding motif and this loop (ANT104-116) inhibited the ANT Vpr interaction (FIG. 1C), presumably via direct association with Vpr52-96 (insert in FIG. 1D).

Neither a topologically-related peptide motif derived from the human phosphate carrier nor mutated and scrambled versions of ANT104-116 (control peptides in FIG. 1C) had such inhibitory effects. ANT104-116 (but not the control peptides) also prevented Vpr52-96-induced membrane permeabilization of ANT proteoliposomes (FIG. 2C), indicating that, in the context of the lipid bilayer, the effect of Vpr involved a direct interaction with ANT. In planar lipid bilayers, low doses of Vpr52-96 (<1 nM) were incapable of forming channels, unless ANT was present.

ANT and Vpr52-96 cooperated to form discrete channels whose conductance (190±2 pS) (FIG. 3) was much larger than those formed by high doses (80 nM) of Vpr52-96 alone (55±2 pS) (FIG. 3 and S. C. Piller, G. D. Ewart, A. Premkumar, G. B. Cox, P. W. Gage, *Proc. Natl. Acad. Sci. USA* 93, 111-115 (1996)), yet was in the range of those formed by $Ca^{2+}$-treated ANT (N. Brustovetsky, M. Klingenberg, *Biochemistry* 35, 8483-8488 (1996). C. Brenner, et al., *Oncogene* 19, 329-336 (2000). These biophysical experiments demonstrate that ANT and Vpr directly interact in membranes to form functionally competent channel-forming hetero(poly)mers.

EXAMPLE 2

Oxidative Properties of Purified Mitochondria Exposed to Vpr

Figures 4A, 4B:
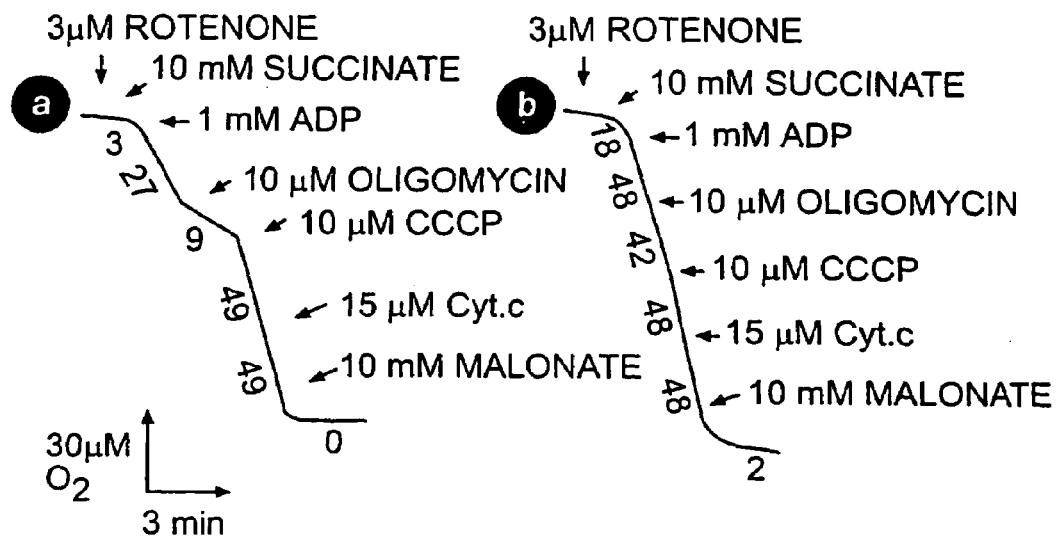

As compared to untreated organelles (FIG. 4A, trace a), purified mitochondria preincubated with Vpr52-96 (FIG. 4A, trace b) exhibited a gross deficiency in respiratory control (RC). Vpr increased succinate oxidation preceding ADP addition and abolished both the inhibitory effect of oligomycin (a specific ATPase inhibitor) and the stimulatory effect of uncoupling by the protonophore carbamoyl cyanide m-chlorophenylhydrazone (CCCP). Thus, Vpr52-96 (but not Vpr1-51) reduced the RC (ratio of oxygen consumption with oligomycin versus CCCP) to a value of 1.1, as compared to 5.3 in control mitochondria (FIG. 4B). The entire Vpr protein (Vpr1-96), and a short peptide corresponding to the minimum "mitochondriotoxic" motif of Vpr (Vpr71-82), (L. G. Macreadie, et al., *Proc. Natl. Acad. Sci. USA* 92, 2770-2774 (1995). I. G. Macreadie, et al., *FEBS Lett.* 410, 145-149 (1997); E. Jacotot, et al., *J. Exp. Med.* 191, 33-45 (2000)) also reduced the RC values (FIG. 4B). Noticeably, the Vpr-induced loss of RC was not associated with a significant decrease of the oxidation rate (FIG. 4A), suggesting that no major loss of membrane-bound cytochrome c occurred upon short-term incubation with Vpr52-96. Accordingly, adding cytochrome c to Vpr52-96-treated mitochondria oxidizing succinate did not stimulate the rate of oxygen uptake (FIG. 4A, trace b). The observation of Vpr-mediated uncoupling of the respiratory chain prompted us to test its capacity to induce IM permeabilization. The IM being essentially impermeable to NADH (P. Rustin, et al., *J. Biol. Chem.* 271, 14785-14790 (1996), no significant oxygen uptake could be measured when NADH was added to control mitochondria (FIG. 5A, trace a). However, addition of Vpr52-96 prompted a significant, NADH-stimulated oxygen consumption (FIG. 5A, trace b). This indicates that Vpr permeabilized IM both to protons (leading to uncoupling, FIG. 4A trace b) and to NADH (FIG. 5A, trace b).

The differential kinetics of inner and outer MMP to NADH and cytochrome c, respectively, were assessed (FIG. 5B). NADH oxidation by mitochondria added with Vpr52-96 was found maximal after 10 min (FIG. 5B). Under similar conditions, Vpr52-96 only induced a marginal access of cytochrome c to cytochrome c oxidase (FIG. 5B). Moreover, the $\Delta\Psi_m$ loss occurred well before cytochrome c release can be detected by immunoblot (FIG. 5C). Hence, Vpr52-96 causes inner MMP well before OM becomes permeable to exogenous cytochrome c. Accordingly, at the ultrastructural level (see below, FIG. 6C), Vpr52-96 treated mitochondria exhibited matrix swelling before OM rupture became apparent.

EXAMPLE 3

Bcl-2-Mediated Inhibition of Vpr Effects on Mitochondria

Figure 6C:
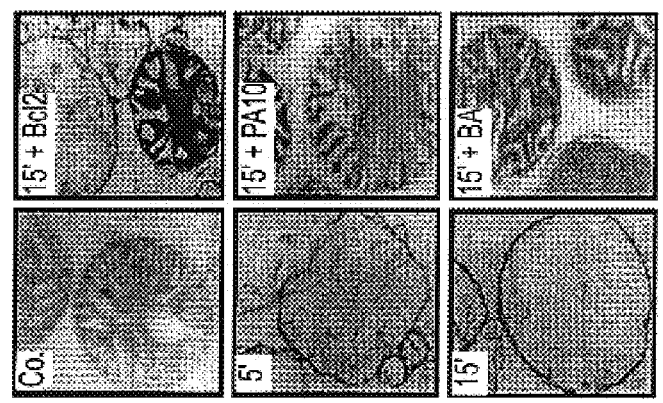
Figure 6A:
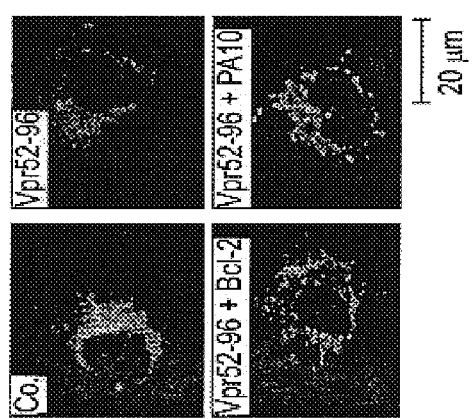
Figure 6B:
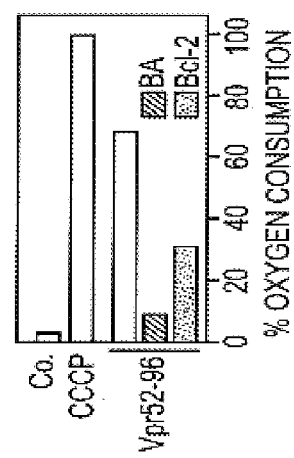
Figure 6D:
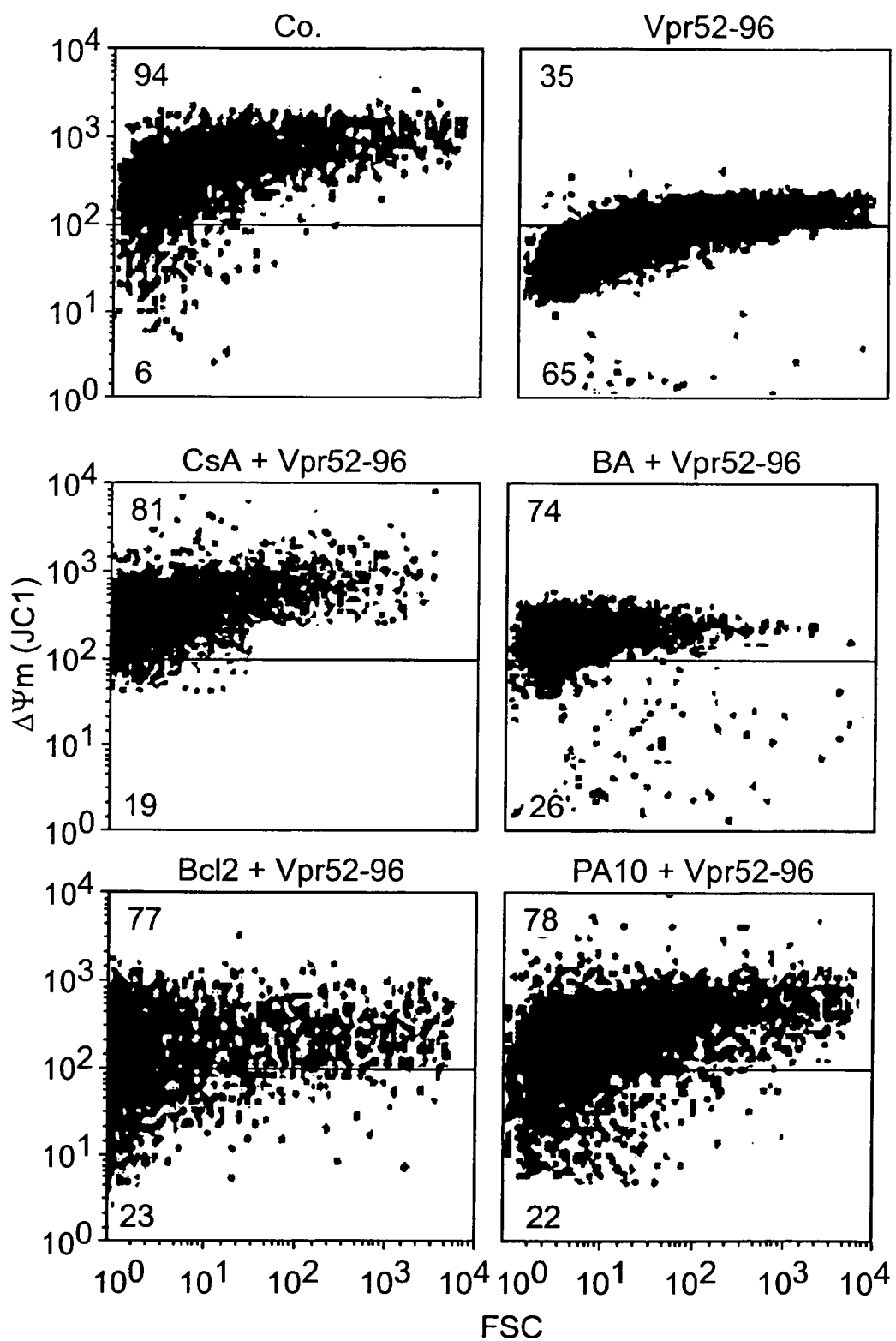
Figure 6E:
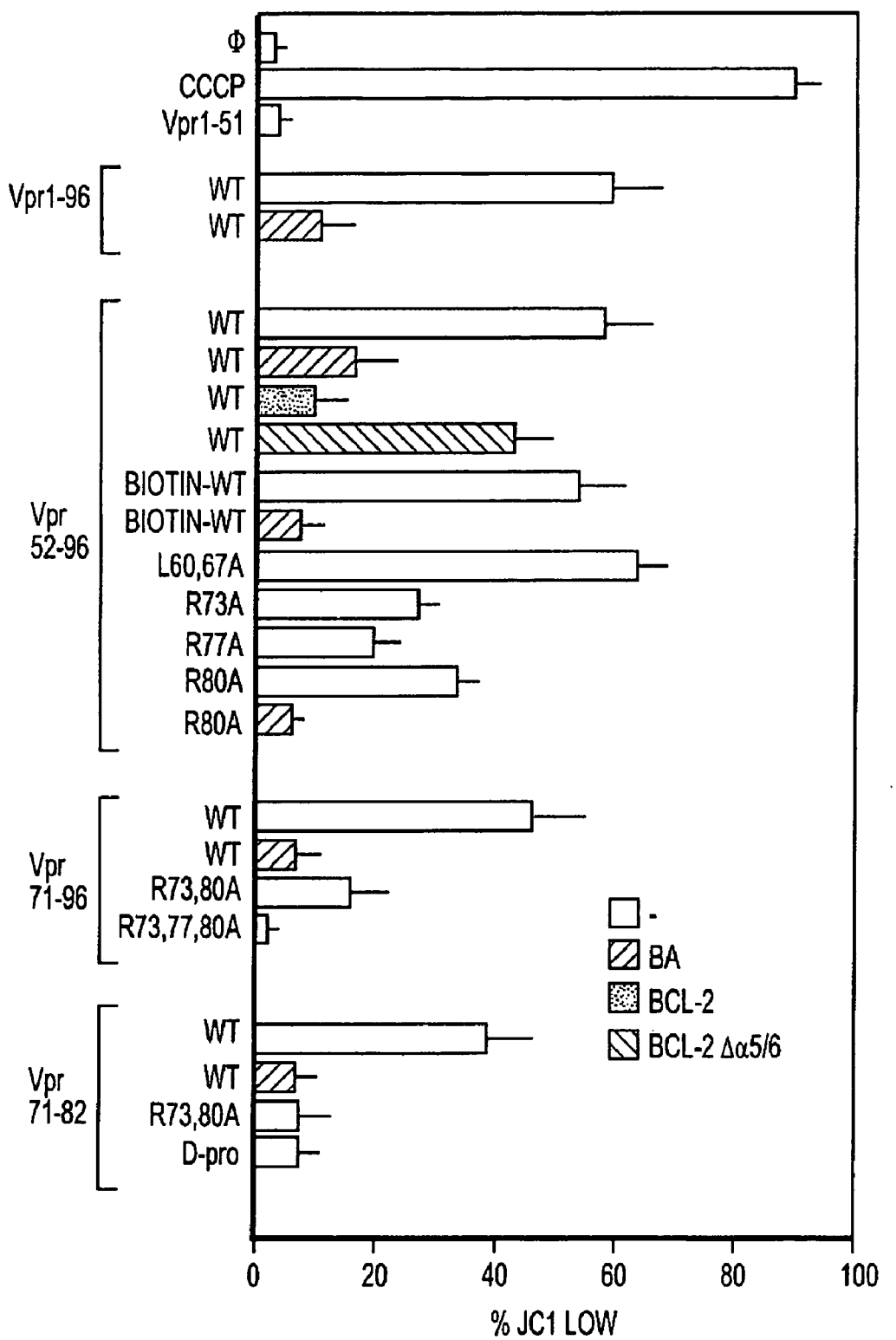

Extracellular addition of Vpr to intact cells induced a rapid $\Delta\Psi_m$ loss, before nuclear condensation occurred. These effects were prevented by microinjection of recombinant Bcl-2 into the cytoplasm (FIG. 6A). Preincubation of purified mitochondria with recombinant Bcl-2 (or the ANT ligand BA) also prevented the Vpr-mediated inner MMP to NADH (FIG. 6B). Concomitantly, both the Vpr-induced matrix swelling (FIG. 6C) and $\Delta\Psi_m$ loss (FIGS. 6D and E) were inhibited by Bcl-2 (but not by Bcl-2$\Delta\alpha$5/6, a deletion mutant lacking the putative pore-forming $\alpha$5 and $\alpha$6 helices, S. Schendel, M. Montal, J. C. Reed, *Cell Death Differ.* 5, 372-380 (1998)), by two pharmacological inhibitors of the PTPC (BA and cyclosporin A; CsA), as well as by the specific VDAC inhibitor Koenig's polyanion (PA10; S. Stanley, J. A. Dias, D. D'Arcangelis, C. A. Mannella, *J. Biol. Chem.* 270, 16694-16700 (1995)). Microinjected PA10 also inhibits the effect of Vpr52-96 on intact cells (FIG. 6A). Binding of Vpr52-96 to purified mitochondria was completely abolished by pre-incubation of the organelles with PA10, partially reduced by BA, but not affected by CsA (FIG. 7B). Thus, Vpr must access mitochondria through VDAC.

Bcl-2 may be expected to prevent Vpr from crossing OM via VDAC (based on the Bcl-2 mediated closure of VDAC) (S. Shimizu, M. Narita, Y. Tsujimoto, *Nature* 399, 483-487 (1999). S. Shimizu, A. Konishi, T. Kodama, Y. Tsujimoto, *Proc. Natl. Acad. Sci USA* 97, 3100-3105 (2000)) and/or to inhibit the Vpr effect on ANT (based on its physical and functional interaction with ANT) (I. Marzo, et al., *Science* 281, 2027-2031 (1998); C. Brenner, et al., *Oncogene* 19, 329-336 (2000); M. Narita, et al., *Proc, Natl. Acad. Sci. USA* 95, 14681-14686 (1998)). Although recombinant Bcl-2 strongly reduced the Vpr52-96-induced matrix swelling (FIG. 6C) and $\Delta\Psi_m$ loss (FIGS. 6D and E), it failed to impair the binding of Vpr52-96 to purified mitochondria (FIG. 7B). The differential inhibitory effects of PA10 and Bcl-2 on the Vpr-ANT interaction was confirmed in a distinct experimental system. PA10 fully abolished the affinity-mediated purification of ANT using biotinylated Vpr52-96 (FIG. 7C), provided that its effect was assessed on intact mitochondria (in which Vpr52-96 has to cross OM to reach ANT). In contrast, PA10 did not affect the Vpr52-96-mediated purification of ANT from triton-solubilized mitochondria (in which ANT is readily accessible to Vpr52-96). In the same conditions, Bcl-2 reduced the Vpr52-96-mediated recovery of ANT, irrespective of its addition to intact or solubilized mitochondria (FIG. 7C). Thus, Bcl-2 does not interfere with the (PA10 inhibited) VDAC-mediated conduit allowing Vpr52-96 to pass OM.

EXAMPLE 4

Bcl-2-Mediated Inhibition of the Vpr-ANT Interaction

Figure 8C:
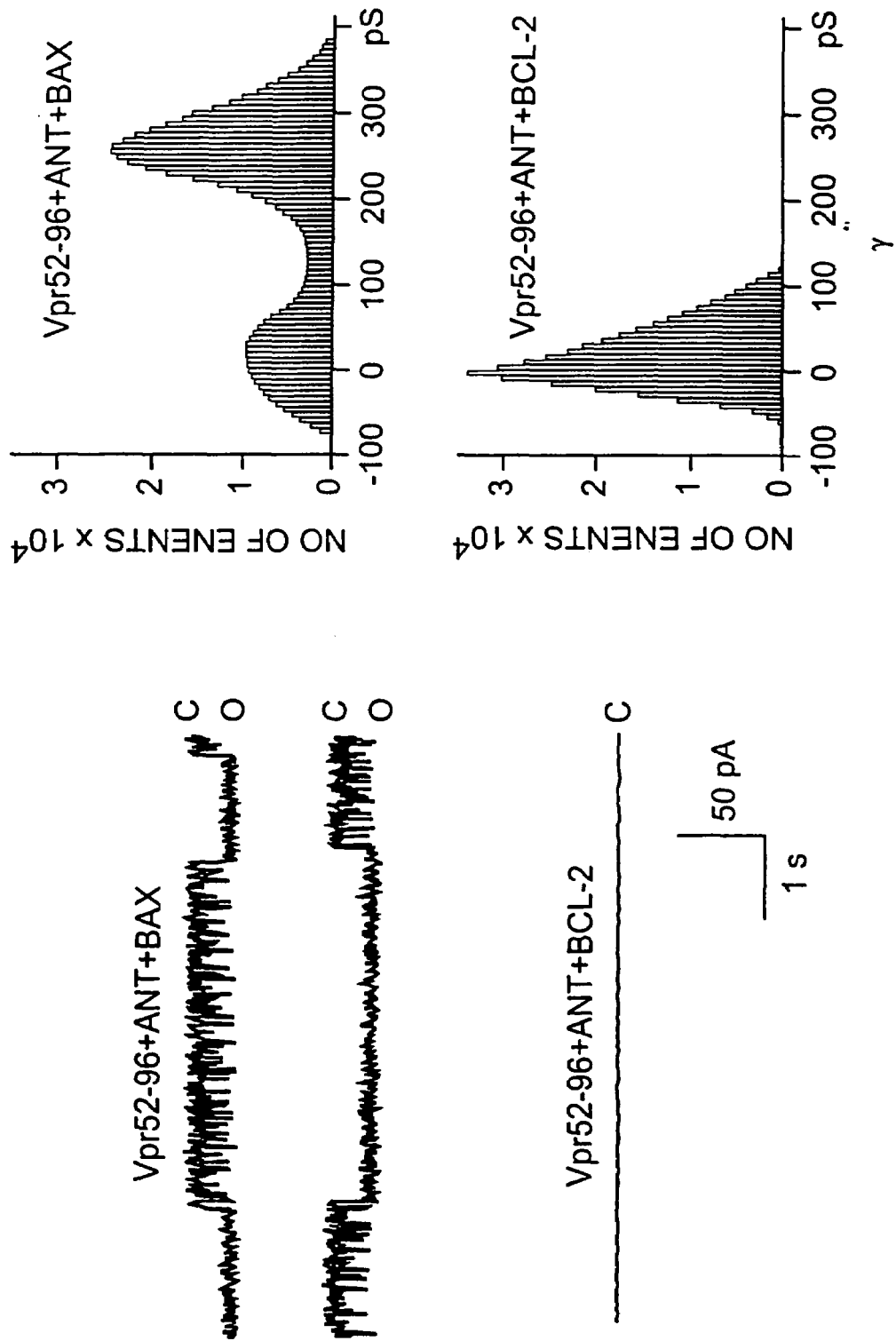

A further series of experiments indicated that Bcl-2 modulated the physical and functional interaction of Vpr with ANT. Recombinant Bcl-2 (but not Bcl-2 $\Delta\alpha$5/6) reduced Vpr52-96 binding to soluble (FIG. 8A) or membrane-associated (FIG. 8B) ANT. Since Bcl-2 did not bind Vpr52-96, inhibition of the Vpr/ANT binding is likely due to a direct Bcl-2/ANT interaction (I. Marzo, et al., *Science* 281, 2027-2031 (1998); C. Brenner, et *Oncogene* 19, 329-336 (2000)). Accordingly, Bcl-2 abolished the formation of Vpr52-96 induced channels in ANT-containing lipid bilayers. In contrast, in the same conditions Bax exacerbates the conductance of Vpr52-96-ANT channels to a mean value of 245±2S (as compared to 190±2 for Vpr52-96-ANT without any further addition) (FIG. 8C).

EXAMPLE 5

Double Test Protocol

1. Purification of ANT. ANT is purified from rat heart and reconstituted in liposomes according to the protocol described by Brenner et al., Oncogene, 2000.

2. Reconstitution of ANT in liposomes. ANT (0.03 mg/ml) is incorporated in liposomes composed of phosphatidylcholine and cardiolipine (PC:CL; 45:1; W: w; and 300 ng ANT per mg of lipids) in the presence of 0.3% n-octyl-β-D-pyranoside for 2 min. at room temperature. If need be, other proteins or compounds are added at this stage during incorporation (e.g., Bcl-2, Bax). Then, the detergent is eliminated by dialyzing, overnight, the liposomes against the buffer 10 mM HEPES, 125 mM sucrose, pH7.4 at 4° C. (e.g.: about 11 of buffer per 1 ml liposomes).

3. Pore function test. The liposomes are charged with 1 mM of 4-UMP (4-methylumbelliferylphosphate) in 10 mM KCl by sonication (50 W, 22 sec). The proteoliposomes are then separated on a Sephadex G25 column to eliminate the non-encapsulated compounds, the elution being performed using the buffer 10 mM HEPES, 125 mM sucrose, pH7.4 at room temperature. In a microplate with 96 wells, 25 μl of liposomes are put in each well.

25 μl of product to be tested are added and incubated for 30-60 min. with different compounds (e.g.: 30 min. for Vpr 52-96; 60 min. for a non-peptide compound) at room temperature. Then, alkaline phosphatase (5 μl/ml) and 150 μl of the reaction buffer 10 mM HEPES, 125 mM sucrose, 0.5 mM MgCl2, pH 7.4 are added. The plate is incubated for 15 min. while being shaken at 37° C. to allow the enzymatic conversion of 4-UMP to 4-umbelliferone (4-UM). The reaction is stopped by adding 150 μl Stop buffer (10 mM HEPES-NaOH, 200 mM EDTA, pH 10). The fluorometric determination of 4-UM is performed (excitation: 365 nm; emission 450+-5 nm). In each experiment, samples of non-treatment of liposomes, of encapsulation of 4-UMP, and of maximum salting out of 4-UMP are created and permit the results to be expressed as a percentage of salted-out 4-UMP.

4 Antiport function test. The liposomes are charged with 1 mM of ATP (4-methylumbelliferylphosphate) in some 10 mM KCl by sonication (50 W, 22 sec). The proteoliposomes are then separated on a Sephadex G25 column to eliminate the non-encapsulated compounds, with elution being performed with some 10 mM HEPES buffer solution, 125 mM sucrose, pH7.4 at room temperature. In a microplate with 96 wells, 25 μl of liposomes are put in each well.

25 µl of product to be tested are added and incubated for 30-60 min. (e.g.: 30 min. for Vpr 52-96; 60 min for a non-peptide compound) at room temperature. Then, 25 µl luciferase (HS II Boerhinger kit) are added, and the emitted light is immediately measured. The results are expressed as a percentage by comparison to the maximum ATP exported in response to an addition of 400 µl to the exterior of the liposomes.

5. Note: Proteoliposomes charged with 4-UMP and KCl with the objective of determining the pore function will freeze at −20° C., but those charged with ATP and KCl to determine the translocator function will not.

REFERENCES

The following references are specifically incorporated by reference in their entirety.

Brenner C, Cadiou H, Vieira H L, Zamzami N, Marzo I, Xie Z, Leber B, Andrews D, Duclohier H, Reed J C, Kroemer G (2000) Bcl-2 and Bax regulate the channel activity of the mitochondrial adenine nucleotide translocator. Oncogene, 19:329-36.

Costantini P, Belzacq A S, Vieira H L, Larochette N, de Pablo M A, Zamzami N, Susin S A, Brenner C, Kroemer G (2000) The critical oxidation of a thiol residue of the adenine nucleotide translocator triggers the opening of a Bcl-2 independent permeability transition pore and apoptosis. Oncogene, 19:307-14.

Zamzami N, El Hamel C, Maisse C, Brenner C, Munoz-Pinedo C, Belzacq A S, Costantini P, Vieira H, Loeffler M, Molle G, Kroemer G (2000) Bid acts on the permeability transition pore complex to induce apoptosis. Oncogene, 19(54):6342-50.

Jacotot E, Ferri K F, El Hamel C, Brenner C, Druillennec S, Hoebecke J, Rustin P, Metivier D, Lenoir C, Geukens M, Vieira H L, Loeffler M, Belzacq A S, Briand J P, Zamzami N, Edelman L, Xie Z H, Reed J C, Roques B P, Kroemer G (2001) Control of mitochondrial membrane permeabilization by adenine nucleotide translocator interacting with HIV-1 viral protein rR and Bcl-2. J Exp Med, 193(4):509-19.

Belzacq A S, Vieira H L, Xie Z H, Reed J C, Kroemer G, Brenner C. ANT as a vital antiporter and a lethal pore. Regulation by Bcl-2 like proteins. In preparation Belzacq A S, Dallaporta B., El Hamel C., Vieira H L, Marchetti P., Reed J C, Kroemer G, Brenner C. Three chemotherapeutic agents act on ANT to permeabilize mitochondrial membranes during apoptosis. In preparation Ferri K F, Jacotot E, Blanco J, Este J A, Kroemer G (2000). Mitochondrial control of cell death induced by HIV-1-encoded proteins. Ann N Y Acad. Sci. 926:149-64.

Marchetti P, Zamzami N, Joseph B, Schraen-Maschke S, Mereau-Richard C, Costantini P, Metivier D, Susin S A, Kroemer G, Formstecher P (1999). The novel retinoid 6-[3-(1-adamantyl)-4-hydroxyphenyl]-2-naphtalene carboxylic acid can trigger apoptosis through a mitochondrial pathway independent of the nucleus. Cancer Res. December 15; 59(24):6257-66.

Larochette N, Decaudin D, Jacotot E, Brenner C, Marzo I, Susin S A, Zamzami N, Xie Z, Reed J, Kroemer G (1999). Arsenite induces apoptosis via a direct effect on the mitochondrial permeability transition pore. Exp Cell Res. June 15; 249(2):413-21.

Ravagnan L, Marzo I, Costantini P, Susin S A, Zamzami N, Petit P X, Hirsch F, Goulbern M, Poupon M F, Miccoli L, Xie Z, Reed J C, Kroemer G (1999). Lonidamine triggers apoptosis via a direct, Bcl-2-inhibited effect on the mitochondrial permeability transition pore. Oncogene. April 22; 18(16):2537-46.

Fulda S, Scaffidi C, Susin S A, Krammer P H, Kroemer G, Peter M E, Debatin K M (1998). Activation of mitochondria and release of mitochondrial apoptogenic factors by betulinic acid. J. Biol. Chem. December 18; 273(51):33942-8.

Belzacq A-S, Jacotot E, Vieria H L A, Mistro D, Granville D J, Xie Z, Reed J C, Kroemer G, Brenner C (2001). Apoptosis induction by the photosensitizer verteporfin: identification of mitochondrial adenine nucleotide translocator as a critical target. Cancer Research. February 15; 61:1260-1264.

Vieira H L A, Haouzi D, El Hamel C, Jacotot E, Belzacq A-S, Brenner C, Kroemer G (2000). Permeabilization of the mitochondrial inner membrane during apoptosis: impact of the adenine nucleotide translocator. Cell Death and Differentiation. 7:1146-1154.

Vieira H L, Belzacq A S, Haouzi D, Bernassola F, Cohen I, Jacotot E, Ferri K F, El Hamel C, Bartle L M, Melino G, Brenner C, Goldmacher V, Kroemer G (2001). The adenine nucleotide translocator: a target of nitric oxide, peroxynitriate, and 4-hydroxynonenal. Oncogene. July 19; 20(32): 4305-16.

What is claimed is:

1. A method for inhibiting the interaction of human immunodeficiency virus type 1 (HIV-1) viral protein R (Vpr) with adenine nucleotide translocator (ANT) comprising:
    (a) providing isolated mitochondria comprising ANT;
    (b) incubating the isolated mitochondria with a molecule capable of inhibiting the binding of Vpr to ANT;
    (c) incubating the isolated mitochondria with a Vpr fragment capable of binding to ANT; and
    (d) assessing the inhibition of the binding of the Vpr fragment to ANT by the molecule.

2. The method claim 1 wherein step (d) comprises the step of measuring the prevention of channel formation in the mitochondrial membranes.

3. The method claim 1 wherein step (d) comprises the step of measuring the prevention of permeabilization of the mitochondrial membranes.

4. The method of claim 1 wherein said molecule is Bcl-2 or a fragment thereof.

5. The method of claim 1 wherein said molecule comprises the amino acid sequence DKRTQFWRYFAGN (SEQ ID NO:3).

6. A method for inhibiting the interaction of human immunodeficiency virus type 1 (HIV-1) viral protein R (Vpr) with adenine nucleotide translocator (ANT) comprising:
    (a) providing isolated mitochondria comprising ANT;
    (b) incubating the isolated mitochondria with a molecule capable of inhibiting the binding of Vpr to ANT;
    (c) incubating the isolated mitochondria with full-length Vpr capable of binding to ANT; and
    (d) assessing the inhibition of the binding of Vpr to ANT by the molecule.

7. The method of claim 1 wherein the Vpr fragment comprises amino acids 52-96 of HIV-1 Vpr.

8. A method of screening for molecules that compete with the binding of human immunodeficiency virus type 1 (HIV-1) viral protein R (Vpr) with adenine nucleotide translocator (ANT) comprising:
    (a) providing a Vpr fragment capable of binding to ANT, wherein the Vpr fragment is labeled;
    (b) contacting said Vpr fragment with isolated mitochondria comprising ANT in the presence and absence of a test molecule; and
    (c) assessing the binding of the labeled Vpr to ANT in the presence and absence of the test molecule.

9. A method of screening for molecules that compete with the binding of human immunodeficiency virus type 1 (HIV-1) viral protein R (Vpr) with adenine nucleotide translocator (ANT) comprising:
    (a) providing a full-length Vpr capable of binding to ANT, wherein the Vpr fragment is labeled;
    (b) contacting said Vpr with isolated mitochondria comprising ANT in the presence and absence of a test molecule; and
    (c) assessing the binding of the labeled Vpr to ANT in the presence and absence of the test molecule.

10. The method of claim 8 wherein said fragment comprises amino acids 52-96 of HIV-1 Vpr.

11. The method of claim 8, wherein the test molecule is Bcl-2 or a fragment thereof.

12. The method of claim 8, wherein the test molecule comprises the amino acid sequence DKRTQFWRYFAGN (SEQ ID NO:3).

* * * * *

UNITED STATES PATENT AND TRADEMARK OFFICE
CERTIFICATE OF CORRECTION

PATENT NO. : 7,642,051 B2
APPLICATION NO. : 11/176370
DATED : January 5, 2010
INVENTOR(S) : Jacotot et al.

It is certified that error appears in the above-identified patent and that said Letters Patent is hereby corrected as shown below:

On the title page, item (75), line 6, "Brenner-Jean," should read --Brenner-Jan,--.

On the title page, item (75), line 8, "Margny-les-Compiégne" should read --Margny-les-Compiègne--.

*In claim 2, column 29, line 12, "method claim" should read --method of claim--.

In claim 2, column 29, line 12, "claim 1" should read --claim 1,--.

*In claim 3, column 29, line 15, "method claim" should read --method of claim--.

In claim 3, column 29, line 15, "claim 1" should read --claim 1,--.

In claim 4, column 29, line 18, "claim 1" should read --claim 1,--.

In claim 5, column 29, line 20, "claim 1" should read --claim 1,--.

In claim 7, column 30, line 1, "claim 1" should read --claim 1,--.

In claim 10, column 30, line 25, "claim 8" should read --claim 8,--.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO.        : 7,642,051 B2
APPLICATION NO.   : 11/176370
DATED             : January 5, 2010
INVENTOR(S)       : Jacotot et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this

Sixteenth Day of November, 2010

David J. Kappos
*Director of the United States Patent and Trademark Office*